(12) United States Patent
Stephens et al.

(10) Patent No.: US 9,283,291 B2
(45) Date of Patent: Mar. 15, 2016

(54) METHODS FOR RADIOLABELING MACROMOLECULES

(75) Inventors: Ross Wentworth Stephens, Stirling (AU); Timothy John Senden, Aranda (AU); David Wallace King, Mawson (AU)

(73) Assignee: The Australian National University, Acton, Australian Capital Territory (AU)

( * ) Notice: Subject to any disclaimer, the term of this patent is extended or adjusted under 35 U.S.C. 154(b) by 549 days.

(21) Appl. No.: 12/989,312

(22) PCT Filed: Apr. 23, 2009

(86) PCT No.: PCT/AU2009/000508
§ 371 (c)(1),
(2), (4) Date: Feb. 8, 2011

(87) PCT Pub. No.: WO2009/129577
PCT Pub. Date: Oct. 29, 2009

(65) Prior Publication Data
US 2011/0165069 A1    Jul. 7, 2011

(30) Foreign Application Priority Data

Apr. 24, 2008  (AU) .............................. 2008902063

(51) Int. Cl.
| | | |
|---|---|---|
| A61K 51/12 | (2006.01) | |
| A61K 41/00 | (2006.01) | |
| A61K 51/06 | (2006.01) | |
| A61K 51/08 | (2006.01) | |
| A61K 51/10 | (2006.01) | |

(52) U.S. Cl.
CPC ......... *A61K 51/1251* (2013.01); *A61K 41/0095* (2013.01); *A61K 51/06* (2013.01); *A61K 51/08* (2013.01); *A61K 51/081* (2013.01); *A61K 51/10* (2013.01)

(58) Field of Classification Search
None
See application file for complete search history.

(56) References Cited

U.S. PATENT DOCUMENTS

| | | | |
|---|---|---|---|
| 5,792,241 A | 8/1998 | Browitt | |
| 5,855,547 A | 1/1999 | Chaney | |
| 6,258,338 B1 | 7/2001 | Gray | |
| 6,508,864 B2 | 1/2003 | Day | |
| 6,537,518 B1 | 3/2003 | Gray | |
| 6,803,069 B2 | 10/2004 | Patnaik et al. | |
| 6,977,068 B1* | 12/2005 | Nair et al. | 424/1.11 |
| 6,998,105 B2 | 2/2006 | Ruys et al. | |
| 7,150,867 B2 | 12/2006 | Ruys et al. | |
| 2004/0220135 A1 | 11/2004 | Gray | |
| 2004/0258603 A1 | 12/2004 | Yakobson et al. | 423/445 B |
| 2006/0067939 A1 | 3/2006 | Buzatu et al. | 424/155.1 |
| 2006/0177373 A1 | 8/2006 | Ruys et al. | |
| 2006/0239907 A1 | 10/2006 | Luzzi et al. | 424/1.11 |

FOREIGN PATENT DOCUMENTS

| | | |
|---|---|---|
| WO | WO 99/04826 A1 | 2/1999 |
| WO | WO 99/04827 A1 | 2/1999 |
| WO | WO 2005/018681 A1 | 3/2005 |
| WO | WO 2006/063418 A2 | 6/2006 |
| WO | WO 2006/116798 A1 | 11/2006 |
| WO | WO 2007/136404 A2 | 11/2007 |
| WO | WO 2008/000045 A1 | 1/2008 |
| WO | 2011/033118 A1 | 3/2011 |

OTHER PUBLICATIONS

Aruva et al. Imaging thromboembolism with fibrin-avid 99mTc-peptide: evaluation in swine. 2006 J. Nucl. Med. 47: 155-62.*
Ekrami et al. Disposition of positively charged Bowman-Birk protease inhibitor conjugates in mice: influence of protein conjugate charge density and size on lung targeting. 1995 J. Pharm. Sci. 84: 456-461.*
Lobov et al. Cationised radiolabelled nanoparticles for perfusion imaging of the lungs. 2013 Biomaterials 34: 1732-1738.*
Herba et al., "Hepatic Malignancies: Improved Treatment with Intraarterial Y-90;" *Radiology* 169(2):311-314, 1988.
Berge et al., "Pharmaceutical Salts," *Journal of Pharmaceutical Sciences* 66(1):1-19, Jan. 1977.
Ekman et al., "Collection of Aerosols in a Venturi Scrubber," *Industrial and Engineering Chemistry* 43(6):1358-1363, 1951.
Garrean et al., "Complete eradication of hepatic metastasis from colorectal cancer by Yttrium-90 SIRT," *World J. Gastroenterol* 13(21):3016-3019, Jun. 7, 2007.
Gray et al., "Regression of Liver Metastases Following Treatment With Yttrium-90 Microspheres," *Aust. N.Z. J. Surg.* 62:105-110, 1992.
Hede, "Radioactive "Seed" Implants May Rival Surgery for Low-Risk Prostate Cancer Patients," *JNCI* 99:1507-1509, 2007.
Kotzerke et al., "PET aerosol lung scintigraphy using Galligas," *Eur J Nucl Med Mol Imaging* 37:175-177, 2010.
Lerman et al., "Lymphoscintigraphic sentinel node identification in patients with breast cancer: the role of SPECT-CT," *Eur J Nucl Med Mol Imaging* 33:329-337, 2006.
Liu et al., "In vivo biodistribution and highly efficient tumour targeting of carbon nanotubes in mice," *Nature Nanotechnology* 2:47-52, Jan. 2007.
Michalik et al., "Aerosol Preconcentration on a Liquid Electrode," *Talanta* 28:43-47, 1981.
Nair et al., "*Thrombo Trace*, a new diagnostic agent with high specificity to bind fibrin in vivo," *Blood Coagulation and Fibrinolysis* 9(7):716-717, 1998.
Sarin et al., "Accelerated partial breast irradiation using multicatheter brachytherapy," *Nature Clinical Practice Oncology* 4(7):382-383, Jul. 2007.

* cited by examiner

*Primary Examiner* — Michael G Hartley
*Assistant Examiner* — Jennifer Lamberski
(74) *Attorney, Agent, or Firm* — Seed IP Law Group PLLC

(57) ABSTRACT

The present invention relates to a method for preparing a radiolabeled macromolecule, the method comprising contacting a macromolecule with a carbon encapsulated nanoparticle composite having a radioactive particulate core in an aqueous medium comprising a pH selected to promote short-range attractive forces between the nanoparticles and the macromolecule by attenuating repulsive electrostatic forces.

8 Claims, 9 Drawing Sheets

METHODS FOR RADIOLABELING MACROMOLECULES

CROSS REFERENCE TO RELATED APPLICATION

This application claims the benefit of Australian Provisional Patent Application No. 2008902063 filed 24 Apr. 2008 which is incorporated herein by reference in its entirety.

FIELD OF THE INVENTION

The present invention relates to methods for the preparation of radiolabelled macromolecules such as biological macromolecules, for example polypeptides. The invention also relates to radiolabelled macromolecules and pharmaceutical and veterinarial preparations thereof. In particular embodiments the invention relates to radiolabelled macromolecules for use in diagnostic tests in vitro and for in vivo diagnostic imaging, regional radiotherapy and targeted radiotherapy.

BACKGROUND OF THE INVENTION

Methods for the production of radiolabelled macromolecules, such as polypeptides, including proteins, peptides and antibodies are known in the art. Typically, traditional methods rely on either simple substitution reactions of subunits of the macromolecule's backbone, e.g. iodination of tyrosine in polypeptides, or organic chemistry to make derivatives which include a chelating entity, capable of avidly retaining radionuclides (usually metal ions), e.g. chelate derivatives of monoclonal antibodies.

For medical applications, the density of radiolabelling of polypeptides such as antibodies is a considerable problem, especially for imaging and therapeutic applications, which call for high levels of radioactivity in very small amounts of material. Also, if one needs to investigate the suitability of a range of different metal radioisotopes, the chelate chemistry has to be customised for each metal. It is therefore desirable to have a method of radiolabelling for macromolecules which can make use of a wide range of different metallic radioisotopes without substantial changes to the chemistry of radiolabelling. This would be especially valuable in medicine where radioisotopes have to be selected from the diversity of those available in order to determine those that are most suitable for different diagnostic and therapeutic applications.

There is a need for improved methods of preparing radiolabeled macromolecules that overcome or avoid one or more disadvantages or limitations of the known methods.

SUMMARY OF THE INVENTION

The present invention aims to provide an improved method for the preparation of radiolabelled macromolecules, in particular radiolabelled biological macromolecules, or provide an alternative to the prior art.

In accordance with a first aspect of the invention, there is provided a method for preparing a radiolabelled macromolecule, the method comprising contacting a macromolecule with a carbon encapsulated nanoparticle composite having a radioactive particulate core in an aqueous medium comprising a pH selected to promote short-range attractive forces between the nanoparticles and the macromolecule by attenuating repulsive electrostatic forces.

In one embodiment the carbon encapsulated nanoparticle composite is FibrinLite.

In one embodiment the carbon encapsulated nanoparticle composite comprises an anionic surfactant. In one embodiment the anionic surfactant is sodium deoxycholate.

In one embodiment the aqueous medium comprises an anionic surfactant. In one embodiment the anionic surfactant is sodium deoxycholate.

In one embodiment the aqueous medium comprises a pH at which the nett charge on the macromolecule is substantially zero.

In one embodiment the aqueous medium comprises a pH substantially equal to the pI of the macromolecule.

In one embodiment the aqueous medium further comprises an electrolyte concentration selected to promote short-range attractive forces between the nanoparticles and the macromolecule by attenuating repulsive electrostatic forces.

In one embodiment the electrolyte is a simple electrolyte selected from the group consisting of Na, K, and Ca.

In one embodiment the simple electrolyte concentration of the aqueous medium is in the range of greater than about 1 millimolar to about 150 millimolar.

In one embodiment the aqueous medium comprises a pH different to the pI of the macromolecule and a simple electrolyte concentration in the range of greater than about 1 millimolar to about 150 millimolar.

In one embodiment the radioactive particulate core comprises a radioactive isotope or radionuclide selected from the group consisting of $^{99m}$Tc, $^{198}$Au, $^{213}$Bi, $^{57}$Co, $^{51}$Cr, $^{64}$Cu, $^{67}$Cu, $^{165}$Dy, $^{169}$Er, $^{59}$Fe, $^{67}$Ga, $^{68}$Ga, $^{153}$Gd, $^{166}$Ho, $^{111}$In, $^{113m}$In, $^{177}$Lu, $^{23}$Na, $^{24}$Na, $^{103}$Pd, $^{81}$Rb, $^{82}$Rb, $^{186}$Re, $^{188}$Re, $^{75}$Se, $^{153}$Sm, $^{117m}$Sn, $^{89}$Sr, $^{201}$Tl, $^{90}$Y, $^{169}$Yb, $^{192}$Ir.

In one embodiment the radioactive particulate core comprises $^{99m}$Tc.

In one embodiment the macromolecule is a biological macromolecule.

In one embodiment the macromolecule is selected from the group consisting of polypeptides, antibodies and fragments and derivatives thereof.

In one embodiment the macromolecule is poly-lysine.

In one embodiment the macromolecule is comprised in or on a catheter, a fibre, a rod or filament, a membrane, a wafer, a mesh or gauze, a porous sponge, a tube or stent, a bead or capsule or microparticles in the form of microbeads of known dimensions, a nanoparticle, a liposome, a glue or a gel.

In one embodiment the method further comprises separating radiolabelled macromolecule from unlabelled macromolecule and or from free nanoparticle composite.

In a second aspect of the invention, there is provided a radiolabelled entity comprising a macromolecule complexed with a carbon encapsulated nanoparticle composite having a radioactive particulate core.

In one embodiment the radiolabelled entity comprises a plurality of distinct macromolecules.

In one embodiment the radiolabelled entity comprises a plurality of distinct radiolabels.

In one embodiment the radiolabelled entity comprises a radiolabel suitable for imaging and a radiolabel suitable for therapeutic application.

In one embodiment the radiolabelled entity comprises a catheter, a fibre, a rod or filament, a membrane, a wafer, a mesh or gauze, a porous sponge, a tube or stent, a bead or capsule or microparticles in the form of microbeads of known dimensions, a nanoparticle, a liposome, a glue or a gel.

In one embodiment the radiolabelled entity is a medical device.

In a third aspect of the invention there is provided a pharmaceutical composition comprising a radiolabelled entity comprising a macromolecule complexed with a carbon encapsulated nanoparticle composite having a radioactive particulate core, together with a pharmaceutically acceptable carrier, adjuvant or excipient.

In one embodiment the macromolecule is selected from the group consisting of polypeptides, antibodies and fragments and derivatives thereof.

In one embodiment the macromolecule is poly-lysine.

In one embodiment the macromolecule is a tissue-specific, organ-specific, cell type-specific, or disease state-specific macromolecule.

In a fourth aspect of the invention there is provided a method of preparing a radiolabelled medical device, the method comprising contacting a macromolecule in complex with a carbon encapsulated nanoparticle composite having a radioactive particulate core with a medical device under conditions suitable for the incorporation of said radiolabelled macromolecule into or onto said medical device.

In a fifth aspect of the invention there is provided a radiolabelled medical device comprising a macromolecule in complex with a carbon encapsulated nanoparticle composite having a radioactive particulate core incorporated into or onto a medical device.

In one embodiment the medical device of any of the second to fifth aspects is selected from a diagnostic device and a therapeutic device.

In one embodiment the device of any of the second to fifth aspects is an is injectable medical device. In one embodiment the macromolecule is incorporated into or onto a microparticle, nanoparticle or liposome.

In one embodiment of any of the second to fifth aspects the medical device comprises a radiolabelled macromolecule comprised in or on a catheter, a fibre, a rod or filament, a membrane, a wafer, a mesh or gauze, a porous sponge, a tube or stent, a bead or capsule or microparticles in the form of microbeads of known dimensions, a nanoparticle, a liposome.

In one embodiment the device of any of the second to fifth aspects is an implantable medical device.

In one embodiment the medical device of any of the second to fifth aspects is a veterinary device.

In a sixth aspect the invention provides a method of radiation therapy of a patient, the method comprising administering to said patient a therapeutically effective amount of a radiolabelled macromolecule, wherein said radiolabelled macromolecule comprises a macromolecule in association with a carbon encapsulated nanoparticle composite having a radioactive particulate core.

In one embodiment the radiation therapy is internal radiation therapy for the lung. For example, the radiation therapy is for the treatment of primary and/or metastatic lung tumours.

In one embodiment the macromolecule is specific for lung.

In one embodiment the macromolecule is poly-lysine. In one embodiment the poly-lysine is of molecular weight about 15 kd to about 30 kd.

In one embodiment the radioactive particulate core comprises at least one of $^{198}$Au, $^{213}$Bi, $^{57}$Co, $^{51}$Cr, $^{67}$Cu, $^{165}$Dy, $^{169}$Er, $^{59}$Fe, $^{67}$Ga, $^{68}$Ga, $^{153}$Gd, $^{166}$Ho, $^{111}$In, $^{113m}$In, $^{177}$Lu, $^{23}$Na, $^{24}$Na, $^{103}$Pd, $^{81}$Rb, $^{82}$Rb, $^{186}$Re, $^{188}$Re, $^{75}$Se, $^{153}$Sm, $^{117m}$Sn, $^{89}$Sr, $^{201}$Tl, $^{90}$Y, $^{169}$Yb, $^{192}$Ir.

In a seventh aspect of the invention, there is provided a method for preparing a macromolecule complexed with an inactive progenitor of a radioisotope, the method comprising contacting a macromolecule with a carbon encapsulated nanoparticle composite having a particulate core comprising an inactive progenitor of a radioisotope in an aqueous medium comprising a pH selected to promote short-range attractive forces between the nanoparticles and the macromolecule by attenuating repulsive electrostatic forces.

In an eighth aspect of the invention there is provided a complex comprising a macromolecule and a carbon encapsulated nanoparticle composite having a particulate core comprising an inactive progenitor of a radioactive isotope.

In a ninth aspect of the invention there is provided a method for radiolabelling a macromolecule, the method comprising the steps of (a) contacting a macromolecule with a carbon encapsulated nanoparticle composite having a particulate core comprising an inactive progenitor of a radioisotope in an aqueous medium comprising a pH selected to promote short-range attractive forces between the nanoparticles and the macromolecule by attenuating repulsive electrostatic forces; and (b) activating said inactive progenitor to generate a radioactive isotope.

In one embodiment of the methods of the invention the aqueous medium further comprises an electrolyte concentration selected to promote short-range attractive forces between the nanoparticles and the macromolecule by attenuating repulsive electrostatic forces.

In one embodiment of the seventh to ninth aspects the inactive progenitor of a radioisotope is stable isotope of boron ($^{10}$B).

In one embodiment of the seventh to ninth aspects the macromolecule is comprised in or on a catheter, a fibre, a rod or filament, a membrane, a wafer, a mesh or gauze, a porous sponge, a tube or stent, a bead or capsule or microparticles in the form of microbeads of known dimensions, a nanoparticle, a liposome.

In one embodiment of the seventh to ninth aspects the method further comprises incorporating said macromolecule into or onto a medical device. In one embodiment the macromolecule is incorporated into or onto a medical device prior to activating. In one embodiment the method further comprises administering said medical device to a subject prior to said activating. In one embodiment said administering comprises implanting said medical device in a subject prior to said activating.

In one embodiment the activating comprises exposing said progenitor to a neutron beam.

In a tenth aspect the invention provides a method of radiation therapy of a patient, the method comprising administering to said patient an amount of a complex comprising a macromolecule and a carbon encapsulated nanoparticle composite having a particulate core comprising an inactive progenitor of a radioactive isotope, wherein said amount is a therapeutically effective amount when said inactive progenitor is activated, and activating said inactive progenitor to generate a radioactive isotope.

In one embodiment said inactive progenitor of a radioactive isotope is boron (boron-10).

In one embodiment said activating comprises exposing said progenitor to a neutron beam.

In an eleventh aspect the invention provides a method of imaging a medical procedure in a patient, the method comprising administering to said patient a complex comprising a macromolecule and carbon encapsulated nanoparticle composite having a radioactive particulate core, and detecting said complex in said subject.

In one embodiment the detecting comprises gamma camera imaging of said radioactivity.

In one embodiment the complex comprises dual labelled macromolecule. In one embodiment the dual labelled macromolecule comprises a radioactive isotope suitable for therapy and a radioactive isotope suitable for imaging.

In a twelfth aspect of the invention there is provided an imaging agent comprising a macromolecule complexed with a carbon encapsulated nanoparticle composite having a radioactive particulate core.

In one embodiment the macromolecule is specific for lung.

In one embodiment the macromolecule is poly-lysine.

In a thirteenth aspect of the invention there is provided a method for diagnosis of a disease or condition affecting blood circulation in the lung of a subject, the method comprising administering to said subject a macromolecule complexed with a carbon encapsulated nanoparticle composite having a radioactive particulate core, and detecting said complex in said subject.

In one embodiment the macromolecule is specific for lung.

In one embodiment the macromolecule is poly-lysine. In one embodiment the poly-lysine is of molecular weight about 15 kd to about 30 kd.

In one embodiment the disease or condition is selected from the group consisting of pulmonary embolism, emphysema, chronic obstructive pulmonary disease (COPD), primary and metastatic lung tumours and infection.

The summary of the invention described above is not limiting and other features and advantages of the invention will be apparent from the following detailed description of the preferred embodiments, as well as from the claims.

BRIEF DESCRIPTION OF THE DRAWINGS

Preferred forms of the present invention will now be described with reference to the accompanying drawings in which.

Binding of Tc-99m FibrinLite (diluted 1:10 into the sodium chloride solutions at the concentrations shown; 100 µL) to polystyrene microwells (Nunc Lockwells™) previously coated with rabbit serum albumin (Sigma A0764). Results are shown for 3 independent experiments with 3 different preparations of FibrinLite.

Figure 5:
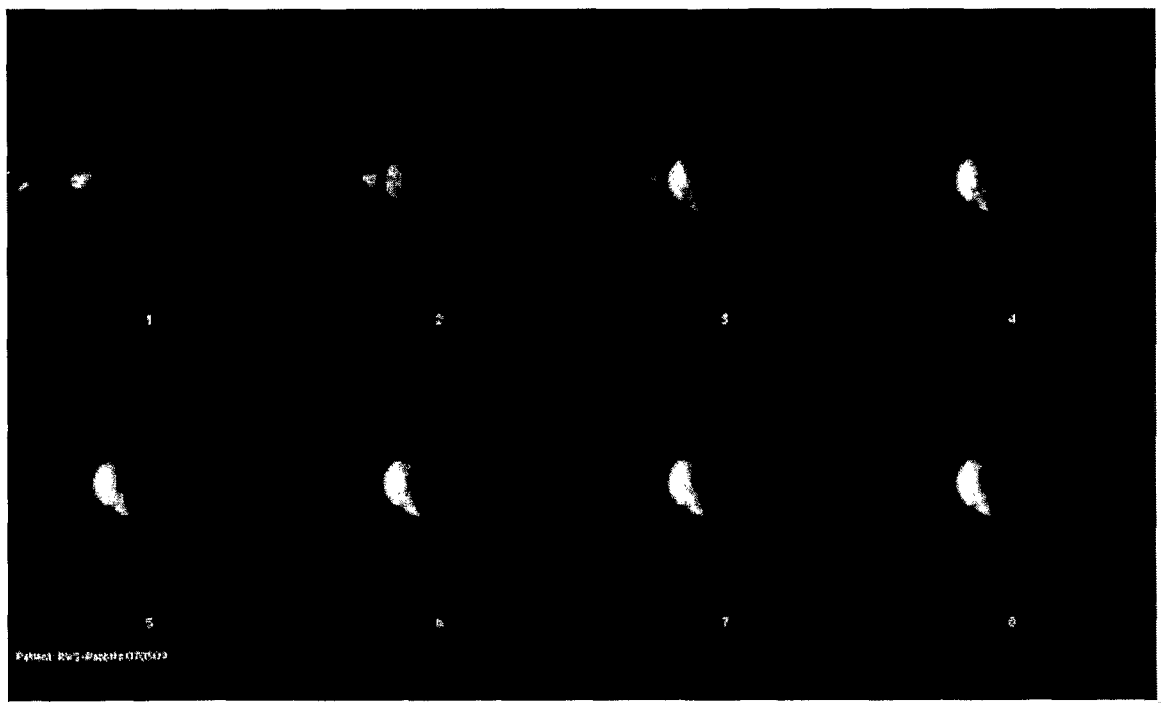

FIG. 5: Circulatory system clearance and biodistribution of uncoated Tc-99m FibrinLite after injection into an ear vein of an anaesthetised rabbit. Acquisition of a sequence of images (Siemens Diacam gamma camera) was initiated immediately upon injection; each frame represents a 30 second interval.

Figure 6:
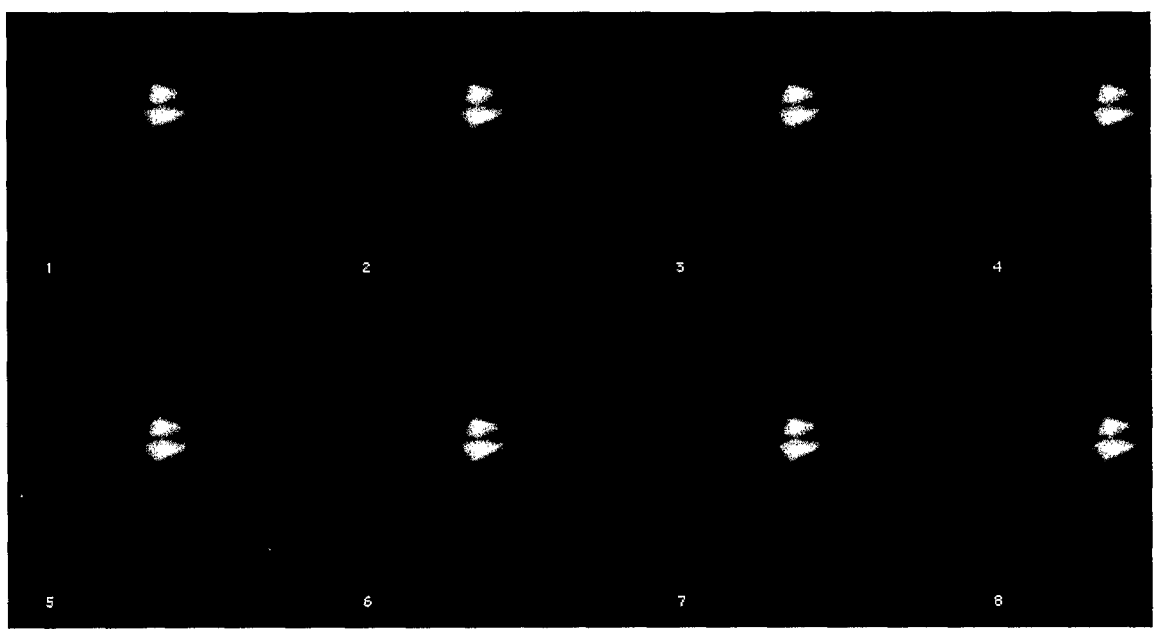

FIG. 6: Circulatory system clearance and biodistribution of poly-lysine (Sigma P4408) treated Tc-99m FibrinLite after injection into an ear vein of an anaesthetised rabbit. Acquisition of a sequence of images (Siemens Diacam gamma camera) was initiated immediately upon injection; each frame represents a 30 second interval.

Figure 7A:
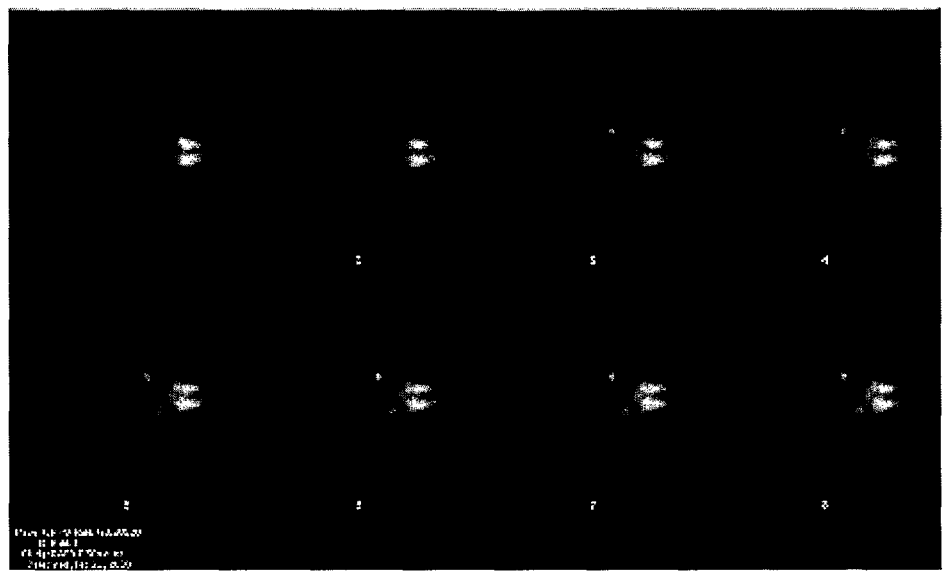

FIG. 7a: Circulatory system clearance and biodistribution of poly-D-lysine (MW 4-15 kd; Sigma P6403) treated Tc-99m FibrinLite after injection into an ear vein of an anaesthetised rabbit. Acquisition of a sequence of images (Siemens Diacam gamma camera) was initiated immediately upon injection; each frame represents a 30 second interval.

Figure 7B:
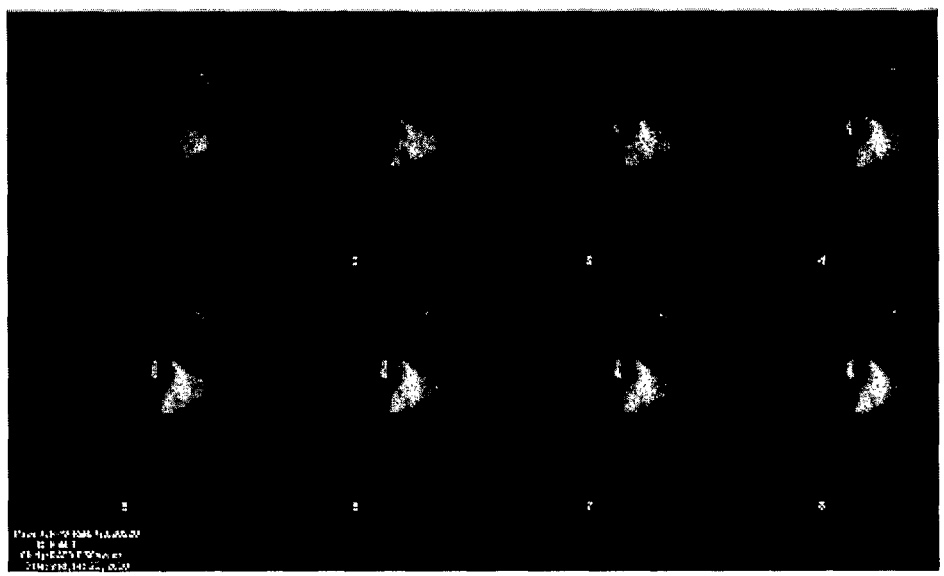

FIG. 7b: Circulatory system clearance and biodistribution of poly-D-lysine (MW 30-70 kd; Sigma P7886) treated Tc-99m FibrinLite after injection into an ear vein of an anaesthetised rabbit. Acquisition of a sequence of images (Siemens Diacam gamma camera) was initiated immediately upon injection; each frame represents a 30 second interval.

ABBREVIATIONS

For convenience, the following abbreviations used in this specification are listed below.

As used herein the term "SPECT" is an abbreviation for single photon computed tomography.

As used herein the term "PET" is an abbreviation for positron emission tomography.

As used herein the term "SIRT" is an abbreviation for selective internal radiation therapy.

As used herein the term "SMPS" is an abbreviation for scanning mobility particle sizing.

As used herein the term "MCE" is an abbreviation for mixed cellulose ester.

As used herein the term "PTFE" is an abbreviation for polytetrafluorethylene.

As used herein the term "DOC" is an abbreviation for sodium deoxycholate.

It will be understood that the description herein regarding the preparation of, and use of, carbon encapsulated nanoparticle composites having a radioactive particulate core (such as FibrinLite nanoparticles) in the preparation of radiolabelled macromolecules applies mutatis mutandis to the use of carbon encapsulated nanoparticle composites having a particulate core comprising an inactive progenitor of a radioisotope, as appropriate as will be recognised by the skilled addressee (such as the use of inactive progenitors rather than active radioisotopes and the activation step in the case of the inactive precursor embodiments).

The term "therapeutically effective amount" as used herein includes within its meaning a non-toxic but sufficient amount of a compound or composition for use in the invention to provide the desired therapeutic effect. The exact amount required will vary from subject to subject depending on factors such as the species being treated, the age, weight and general condition of the subject, co-morbidities, the severity of the condition being treated, the particular agent being administered and the mode of administration and so forth. Thus, for any given case, an appropriate "effective amount" may be determined by one of ordinary skill in the art using only routine methods.

In the context of this specification, the term "comprising" means "including principally, but not necessarily solely". Furthermore, variations of the word "comprising", such as "comprise" and "comprises", have correspondingly varied meanings. Hence, the term "comprising" and variations thereof is used in an inclusive rather than exclusive meaning such that additional integers or features may optionally be present in a composition, method, etc. that is described as comprising integer A, or comprising integer A and B, etc.

In the context of this specification the term "about" will be understood as indicating the usual tolerances that a skilled addressee would associate with the given value.

In the context of this specification, where a range is stated for a parameter it will be understood that the parameter includes all values within the stated range, inclusive of the stated endpoints of the range. For example, a range of "5 to 10" will be understood to include the values 5, 6, 7, 8, 9, and 10 as well as any sub-range within the stated range, such as to include the sub-range of 6 to 10, 7 to 10, 6 to 9, 7 to 9, etc, and inclusive of any value and range between the integers which is reasonable in the context of the range stated, such as 5.5, 6.5, 7.5, 5.5 to 8.5 and 6.5 to 9, etc.

In the context of this specification, the term "plurality" means any number greater than one.

To the extent that it is permitted, all references cited herein are incorporated by reference in their entirety.

DESCRIPTION OF PREFERRED AND OTHER EMBODIMENTS

The present invention will now be described in more detail, including, by way of illustration only, with respect to the examples which follow.

The inventors have discovered that suitable conditions of pH, and optionally of electrolyte concentration, can be selected that facilitate the reduction of repulsive charges between nanoparticle composites of carbon-encapsulated radionuclides and macromolecules and thus enable short-range attractive forces to dominate over repulsive electrostatic forces, such that the nanoparticle composites (such as FibrinLite nanoparticles) become virtually irreversibly bound to or complexed with a macromolecule. The present invention thus relates to a method for the use of nanoparticle composites of carbon-encapsulated radionuclides (such as FibrinLite) for high specific activity radiolabeling of macromolecules capable of attractive hydrophobic, ion correlation or dispersion interactions with the graphite that comprises the external surface of the nanoparticles. In general the macromolecules include biological macromolecules, such as polypeptides, antibodies and the like.

In specific embodiments, the methodology permits high avidity radiolabelling of macromolecules, for example those used in medical applications for diagnosis or therapy, and those used in research applications such as for specific in vitro analysis of biological markers in body fluids or tissue samples, for biodistribution studies of disease markers, e.g. tumour markers, in vivo and for external imaging of other disease sites identified by specific macromolecular targeting vectors, e.g. monoclonal antibodies. The method may also be used to label whole living cells ex vivo, e.g subsets of the peripheral blood cell population, for subsequent injection into the body and tracking by imaging techniques of the organ distribution, or accumulation at disease sites. It will thus be understood that the method of the invention, and products of the method, find use in any situation in which a radiolabelled macromolecule finds use.

In preferred embodiments the high avidity radiolabelling of the macromolecule is substantially irreversible under conditions typically encountered by the labelled macromolecule. Typically, the high avidity radiolabelling of the macromolecule is such that there is less than about 10% dissociation under in vivo conditions.

U.S. Pat. No. 6,977,068 entitled "Method for detection of fibrin clots" dated 20 Dec. 2005 to Nair et al. describes methods for the use of carbon-encapsulated radionuclide nanoparticles in the detection of fibrin clots. International Patent Application No. PCT/AU2006/000554 filed 28 Apr. 2006 and published as WO 2006/116798 A1, entitled "A method of forming an injectable radioactive composition of a carbon encapsulated radioactive particulate" describes a process for the production of an injectable formulation of carbon encapsulated nanoparticles. The process described therein can be referred to as "FibrinLite process" and the nanoparticles so-produced may be referred to as "FibrinLite". To the extent permitted, the entire contents of both U.S. Pat. No. 6,977,068 and PCT/AU2006/000554 (WO 2006/116798) are incorporated herein by reference.

It will be understood that a person skilled in the art will be aware that methods of producing an aqueous dispersion of carbon encapsulated nanoparticle composites may include a step of aqueous capture of a radioactive aerosol and that this step may be achieved in a number of ways. For example, the step of aqueous capture of a radioactive aerosol used to make carbon encapsulated nanoparticle composites may include but not be limited to the following:

1. Collection of the aerosol in a Venturi scrubber, for example according to the method of Ekman and Johnstone, published in Industrial and Engineering Chemistry (1951) volume 43, part 6, pages 1358 to 1363.

2. Concentration of the aerosol on a liquid electrode, for example according to the method of Michalik and Stephens, published in Talanta (1981) volume 28, part 1, pages 43 to 47.

3. Use of a cyclone device, for example the cyclone device disclosed by P. J. Day in U.S. Pat. No. 6,508,864 (published on Jan. 21, 2003).

In one exemplary embodiment the carbon encapsulated nanoparticle composites may be prepared using the process described in PCT/AU2006/00054, wherein the process involves capture of the radioactive aerosol in water utilising a Browitt precipitator described in U.S. Pat. No. 5,792,241 the entire contents of which are herein incorporated by reference.

As described herein the present inventors have discovered a method for using the carbon encapsulated nanoparticles (such as FibrinLite nanoparticles) that can provide high specific radioactivity and high avidity radiolabeling of macromolecules.

By providing a method by which radiolabelled macromolecules may be prepared using FibrinLite nanoparticles, the present inventors take advantage of the carbon encapsulation process (see PCT/AU2006/000554) which wraps the metallic isotope in a carbon cage, so that it becomes physically isolated from contact with its external environment, an especially valuable property for the particles and hence the macromolecule, particularly when they are to be used in vivo. The potential for leaching and bio-uptake of the radioactive metal ions in vivo of the radiolabelled macromolecule is virtually non-existent because only the carbon exterior of the nanoparticle composite is exposed to the biological environment in vivo.

Macromolecules and Uses in medicine

Through the present invention methods for the use of nanoparticle composites of carbon encapsulated radionuclides (FibrinLite) for high specific activity radiolabelling of macromolecules preferably biological macromolecules such as polypeptides, including proteins, peptides, antibodies and polycations such as poly-lysine are provided. The present invention relates to methods by which the nanoparticles can be coated with the macromolecule(s) such as polypeptides, proteins, and antibodies, so that the resulting particles have a core of high specific activity of detectable radiolabel as well as tightly bound polypeptide. The polypeptide may be selected from a large diversity of biological ligands that have specific interactions with tissue or cell-surface markers, antigens, receptors, and binding sites.

The radiolabelled macromolecule may be used to accumulate a therapeutic isotope at a pre-determined disease site in vivo, based on the specific biological interaction that the macromolecule has with a disease marker. For example a radiolabelled monoclonal antibody with specificity for a tumour marker may be used to accumulate a cytotoxic dose of a therapeutic isotope within a tumour. In such applications the radioisotope is typically selected from those that have short-range, high-energy emissions capable of killing proliferating cells, such as $^{153}$Sm, $^{90}$Y, $^{125}$I, $^{131}$I, $^{192}$Ir, $^{103}$Pd, $^{111}$In, $^{166}$Ho. An example of this type of tumour radiotherapy is provided by Kaminski, *New England Journal of Medicine* 352:441-449 (2005).

Another method of use of the radiolabelled macromolecules is in medical imaging, such as for diagnosis of a disease or condition. Where the disease or condition is specific to, localised in, or affects a particular tissue, organ or cell type, the macromolecule may be selected for specificity to that tissue, organ or cell type or for specificity to a characteristic of the disease or condition, such as altered expression of a biological molecule(s) in affected compared to unaffected states. For example, as demonstrated herein, FibrinLite in complex with poly-lysine is selective for lung tissue and when administered to a subject will preferentially target the lung. In this manner the poly-lysine coated FibrinLite can be used as an imaging agent for the diagnosis of disease or conditions affecting blood circulation in the lung, such as pulmonary embolism, emphysema, chronic obstructive pulmonary disease (COPD), primary and metastatic lung tumours and infection. The imaging permits the physician or technician to form an image of the circulation system of the lung, for example to identify the absence or presence of a disease state, including for example the severity thereof, the progression thereof, the effectiveness of a treatment thereof.

Another method of use is in the form of radiolabelled nanoparticles for intra-operative imaging such as for the purpose of identification and localization of lymph nodes draining a tumour site, e.g. imaging of sentinel nodes in breast cancer patients. In this technique radiolabelled nanoparticles are injected directly into a tumour site, from where they migrate in the interstitial fluid and enter the lymph draining a tumour site, ultimately to accumulate in the nearest (sentinel) lymph node. The isotope in this case would be selected from those most suitable for imaging, such as $^{99}$Tc. [Lerman et al, *Eur J Nucl Med Mol Imaging* 33:329-337 (2006)]. In this application the particles are small enough that they will diffuse in the interstitial fluid in a tissue and be collected in the lymph drainage; accordingly nanoparticles rather than microparticles are typically used.

Another method of use is in boron neutron capture therapy (BNCT). This method involves the accumulation of a stable isotope precursor (or progenitor), such as boron-10, at the site of disease, typically a tumour site such as glioblastoma, and the application of a beam of low energy neutrons to the accumulated isotope. Boron-10 in or adjacent to the tumor cells disintegrates after capturing a neutron and the high energy heavy charged particles produced destroy only the cells in close proximity to it, primarily cancer cells, leaving adjacent normal cells largely unaffected. The present invention provides that a macromolecule, in free form such as in solution or dispersion, or comprised in or on a medical device, may be prepared with a high avidity and or high density of radioactive precursor, such as a stable isotope of boron to permit improved delivery and concentration of the isotope at the treatment site.

It is to be noted that reference herein to use in medicine will be understood to be equally applicable to human and non-human, such as veterinary, applications. Hence it will be understood that, except where otherwise indicated, reference to a patient, subject or individual means a human or non-human, such as an individual of any species of social, economic or research importance including but not limited to lagomorph, ovine, bovine, equine, porcine, feline, canine, primate and rodent species.

Similarly, it is to be noted that reference herein to a "medical" device will be understood to be equally applicable to a medical device suitable for use in human and non-human, such as veterinary, applications.

As used herein the term "device" will be understood to include devices which may be used in therapy, including preventative and treatment of an actual condition or symptom, and those which may be used in diagnosis, including where the diagnosis is performed on or in the body of a patient and where the diagnosis is performed on or with a sample obtained from the body of a patient. Accordingly, the term "device" as used wherein includes therapeutic devices and diagnostic devices.

As used herein "diagnosis" will be understood to include investigative procedures performed in circumstances where a disease or condition is suspected, such as for initial investigation, prognosis, progression of a disease or condition whether in the presence or the absence of therapy, and in circumstances where no such suspicion exists but where investigation is desired, such as for the purposes of health checks, population screening or research.

Radioactive Isotopes and Inactive Precursors

The skilled addressee will appreciate that, because the method of the present invention permits the FibrinLite particles to be used in labelling a macromolecule, any radioisotope that may be incorporated in the FibrinLite nanoparticle may therefore be used as the radioisotope by which a macromolecule is radiolabelled. Similarly, any inactive progenitor of a radioactive isotope that may be incorporated in the FibrinLite nanoparticle and that is capable of activation to generate a radioisotope may be used in the preparation of an inactive precursor-labelled macromolecule and hence in preparation of a radiolabelled macromolecule.

As described in PCT/AU2006/000554 a diverse range of radioisotopes may be incorporated in FibrinLite nanoparticles, including those that emit gamma radiation, such as Tc-99m, Ga-67; those that emit beta radiation, such as Y-90; those that emit alpha radiation, such as Bi-213; and those that emit positron radiation, such as Cu-64. Any suitable metallic radioactive isotope may be utilised, including $^{198}$Au, $^{64}$Cu, $^{213}$Bi, $^{57}$Co, $^{51}$Cr, $^{165}$Dy, $^{169}$Er, $^{59}$Fe, $^{67}$Ga, $^{68}$Ga, $^{153}$Gd, $^{166}$Ho, $^{111}$In, $^{113m}$In, $^{177}$Lu, $^{23}$Na, $^{24}$Na, $^{103}$Pd, $^{81}$Rb, $^{82}$Rb, $^{186}$Re, $^{75}$Se, $^{153}$Sm, $^{117m}$Sn, $^{89}$Sr, $^{201}$Tl, $^{90}$Y, $^{169}$Yb, $^{192}$Ir. Similarly any suitable inactive precursor of a radioisotope may be utilised in relevant embodiments, including $^{10}$B.

The range of isotopes that may be used in the FibrinLite nanoparticles and hence in the methods of the present invention, include those that are ideally suited for diagnostic imaging applications, such as single photon computed tomography (SPECT) using Tc-99m or Ga-67, and positron emission tomography (PET) using Cu-64 or Zr-89. Additionally, included also are isotopes suitable for targeted radiotherapy as described above, such as those already in use for ablation of certain types of tumours, for example Y-90 labelled monoclonal antibodies used for treatment of lymphomas. The present invention provides an alternative method by which such labelled entities and others may be prepared, as suitable for diagnostic imaging of tumours or as suitable for tumour therapy.

Typically the radioisotopes most suitable for imaging may not be the most suitable for therapy. The present invention also includes the possibility of dual labelling of macromolecules, in which one isotope is selected for optimal imaging, and the other isotope for optimal therapy. This composite is intended to allow more reliable dosimetry in the use of the beads for tumour therapy, using the imaging to facilitate localisation of the therapeutic dose and also to enable external estimation of the dose of therapeutic isotope that has been delivered to a given organ site, and the dose delivered to a tumour versus the normal host tissue. A dual labelled device may be prepared by any suitable method, such as by contacting a device with two distinctly labelled macromolecules or contacting a device with a macromolecule composition labelled with two distinct radiolabels; in which case for the latter the dual labelled macromolecule composition may be prepared using two differently labelled FibrinLite compositions (simultaneously or sequentially) or by preparing a single FibrinLite composite which itself is dual-labelled. Typically two separate preparations of FibrinLite are prepared, using two different isotopes, and a mixture of the two preparations is used to radiolabel the macromolecule. By changing the ratio of the two preparations in the mixture, adjustment can be made of the therapeutic activity while maintaining a suitable level of activity for imaging.

For some applications, typically for some therapeutic applications, it may be advantageous to generate a radioactive isotope locally in a target organ site after injection and local accumulation of macromolecules bearing the inactive progenitor. Exposure of the organ site to a narrow neutron beam may then activate the progenitor to form a therapeutic isotope. In this embodiment the nanoparticles used for loading the macromolecule may comprise an encapsulated stable metallic isotope, e.g. boron-10 ($^{10}$B), that is the inactive progenitor of a radioactive isotope that may be activated by exposure to a suitable activator, such as a neutron beam to form a therapeutic isotope in situ. By this means very short-lived, high-energy isotopes, e.g. alpha-emitters, may be more safely and efficaciously generated locally for the purpose of tumour ablation.

Formulation of Nanoparticle Composites for Radiolabeling Macromolecules

The carbon encapsulated nanoparticle composite having a radioactive particulate core (referred to herein as "FibrinLite", e.g., an aqueous dispersion of carbon encapsulated $^{99m}$Tc, $^{113m}$In, $^{111}$In, $^{198}$Au, $^{64}$Cu, $^{213}$Bi, $^{57}$Co, $^{51}$Cr, $^{165}$Dy, $^{169}$Er, $^{59}$Fe, $^{153}$Gd, $^{166}$Ho, $^{177}$Lu, $^{103}$Pd, $^{81}$Rb, $^{82}$Rb, $^{186}$Re, $^{188}$Re, $^{75}$Se, $^{153}$Sm, $^{117m}$Sn, $^{89}$Sr, $^{201}$Tl, $^{90}$Y, or $^{169}$Yb nanoparticles having a diameter of 10 to 500 nanometers) may be prepared according to PCT/AU2006/000554 entitled "A method of forming an injectable radioactive composition of a carbon encapsulated radioactive particulate" (published as WO 2006/116798), the entire contents of which are herein incorporated by reference. Thus the composite may typically be prepared as a neutral or slightly acid pH, stable aqueous dispersion of nanoparticles comprising carbon-encapsulated radionuclide.

The dispersion of nanoparticles typically may contain a very low (for example, in the range of about 1 micromolar to about 20 micromolar, typically about 10 micromolar) concentration of an anionic surfactant, such as sodium deoxycholate which is compatible with and may be injected into, the blood circulation of a living subject. Typically, in therapeutic or in vitro diagnostic applications of the radiolabelled entity, any anionic surfactant approved by regulatory authorities for intravenous use (eg., injection) in humans or animals as the case may be used.

As described in PCT/AU2006/000554 an exemplary radionuclide is Tc-99m. The nanoparticles can each carry tens of thousands or more of isotope atoms in their core, so that very high levels of specific activity can readily be obtained that are well above those obtainable with traditional labelling methods. For FibrinLite, and using Tc-99m as the model encapsulated radioisotope, a Tc-99m loading in the range of from about 1 to about 100 mCi, about 5 to about 100 mCi, about 7.5 to about 95 mCi, about 10 to about 90 mCi, about 15 to about 85 mCi, about 20 to about 80 mCi, about 25 to about 75 mCi, about 30 to about 70 mCi, about 35 to about 65 mCi, about 40 to about 60 mCi, about 45 to about 55 mCi, or about 50 to about 55 mCi may be prepared. A typical preparation of particles can readily be made so as to contain between about 1 and about 30 mCi in 2 mL of aqueous suspension, as desired. From vapour phase characterization of the particles using scanning mobility particle sizing (SMPS), it can be shown that the suspension can contain approximately 50 µg of nanoparticle material, so that the specific activity can be made as high as 600 mCi/mg, or over 22 GBq/mg. The specific activity of the preparation may be adjusted as desired by varying the activity of isotope used to load the crucible in the aerosol generator.

As described in PCT/AU2006/000554 a broad range of suitable radioactive isotopes may be used in the FibrinLite process and thus it will be appreciated that a broad range of isotopes may be used in the methods of the present invention. A specific example isotope is technetium, more specifically $^{99m}$Tc. The solid form of technetium may be sodium pertechnate or any insoluble form of technetium produced during the electrolytic process described in PCT/AU2006/000554, e.g. insoluble oxichlorides. The technetium may be in the form of a radioactive isotope of technetium.

Other metallic radioisotopes or radionuclides may be utilised such as $^{198}$Au, $^{64}$Cu, $^{213}$Bi, $^{57}$Co, $^{51}$Cr, $^{165}$Dy, $^{169}$Er, $^{59}$Fe, $^{66}$Ga, $^{67}$Ga, $^{68}$Ga, $^{153}$Gd, $^{166}$Ho, $^{111}$In, $^{113m}$In, $^{177}$Lu, $^{23}$Na, $^{24}$Na, $^{103}$Pd, $^{81}$Rb, $^{82}$Rb, $^{186}$Re, $^{188}$Re, $^{75}$Se, $^{153}$Sm, $^{117m}$Sn, $^{89}$Sr, $^{201}$Tl, $^{90}$Y, $^{169}$Yb, $^{192}$Ir, $^{94m}$Tc, and $^{89}$Zr. For applications involving the loading of the particles and hence the 'labelling' of the macromolecule or device comprising a macromolecule with an inactive progenitor of a radioisotope, any suitable inactive progenitor may be used. Typically, $^{10}$B may be used.

As described in PCT/AU2006/000554, FibrinLite nanoparticles may be produced as a stable aqueous dispersion with a very low electrolyte concentration, less than the equivalent of 1.0 mM NaCl. Any of the methods described in PCT/AU2006/000554 or derivable there from for the preparation of the FibrinLite particles may be utilised in the preparation of the FibrinLite particles for use in the present invention. In the preferred methods described in PCT/AU2006/000554 this may be achieved by heating the isotope loaded graphite crucible at approximately 1600-1650° C. for 15 seconds to remove carrier sodium chloride before ablation of radioisotope above 2700° C. The boiling point of sodium chloride is only 1413° C., and the Tc-99m radioisotope is not volatile at this temperature. Where alternative radioisotopes are utilized in the methods of the invention the skilled addressee will be able to determine appropriate temperature of ablation, such as by reference to PCT/AU2006/000554.

Aqueous dispersions of FibrinLite nanoparticles made according to PCT/AU2006/000554 do not flocculate, precipitate or sediment on standing for e.g. 48 hours. The dispersion of nanoparticles may contain a very low (for example, in the range of about 1 micromolar to about 20 micromolar, typically about 10 micromolar) concentration of an anionic surfactant, typically sodium deoxycholate which is compatible with and may be injected into, the blood circulation of a living subject (see FIGS. 5 and 6, herein). The FibrinLite nanoparticles may be stored in any appropriate manner, preferably to permit stability of the dispersion, such as by storage in a low concentration of a weakly acidic buffer, such as at a final concentration of 300 micromolar sodium dihydrogen citrate at pH 4.1. The dispersion of nanoparticles is stable, and may be size-fractionated by the use of readily available hydrophilic membrane filters, such as Millipore mixed cellulose ester (MCE) syringe filters, available with porosity of 800, 450 and 220 nm. More than 90% of the radioactivity in a typical FibrinLite nanoparticle preparation will pass through a 800 nm MCE filter, and the same preparation can be shown by thin-layer chromatography to contain typically less than 5% soluble isotope.

Conditions for Radiolabelling Macromolecules Using Fibrinlite Nanoparticles

The nanoparticles so-produced or obtained may be used in the methods of the present invention for radiolabelling of macromolecules.

Hydrophobic interfaces, such as an air-water interface, hydrocarbon-water interfaces and by inference a graphite-water interface as in aqueous FibrinLite suspensions, generally attract a slight predominance of hydoxyl ions in pure water. The result is that these interfaces behave as slightly negatively charged, although the surface potentials are usually very low (tens of millivolts). In the case of FibrinLite, the nanoparticles may also bear increased negative charge on their surface due to adsorption of the anionic surfactant, typically deoxycholate, that is used in their preparation. If the particles and a macromolecule are similarly negatively charged in the same aqueous medium they may weakly repel each other at the tens of nanometers scale when their diffuse double layers of charges overlap. However, the selection of a pH of the aqueous medium in which the nett charge on the macromolecule is substantially zero, such as at the pI of the macromolecule, very rapidly screens this potential such that it offers little energetic barrier to the adsorption and cohesion of particles to a macromolecule in these systems. Such screening, at Debye lengths <10 nm, will produce a situation in which attractive dispersion, ion correlation or hydrophobic forces will usually dominate the total interaction energy of these surfaces. The result is that particles once engaged with the macromolecule will tenaciously adhere to that macromolecule in an essentially irreversible manner. The conditions thereby promote avid binding of the macromolecule and nanoparticle composite. In preferred embodiments the medium in which the contacting occurs may comprise a pH and an electrolyte concentration which promotes the influence of short range attractive forces between the nanoparticles and macromolecule over the long-range electrostatic repulsive forces by diminishing the latter in extent and magnitude. As a result of successful contacting the macromolecule may be described as being associated with or complexed with the nanoparticle composite. The resultant entity may also be referred to as a complex. It is noted that the terms "complex" and "complexed with" in the present context are not intended to imply any particular structural arrangement of the macromolecule and nanoparticle composite other than what occurs as a result of successful contacting in which they become tightly bound.

In the methods of the present invention the FibrinLite nanoparticles may be used to label a macromolecule by contacting the nanoparticles and the macromolecule under conditions of suitable pH and preferably also suitable electrolyte concentration. The inventors have discovered that suitable solution conditions can be selected that facilitate the screening process described above and thus enable short-range attractive forces to dominate over repulsive electrostatic forces, such that the FibrinLite nanoparticles become virtually irreversibly bound to a macromolecule. In view of the disclosure herein it will be appreciated that appropriate and, if desired, optimal, binding conditions, such as pH and electrolyte concentration, can be determined empirically for a desired contacting between nanoparticles and a macromolecule.

The contacting may occur in any suitable medium, although an aqueous medium will usually be preferred. Prior to the contacting the nanoparticles may be prepared in or stored in a suitable storage medium, generally selected to permit stability of the dispersion. Thus the dispersion of nanoparticles may contain a very low (for example, about 10 micromolar) concentration of an anionic surfactant, such as sodium deoxycholate. Prior to the contacting step of the method of the invention, the nanoparticles may be pre-treated to adjust the conditions of the dispersion to favor binding of the nanoparticles and macromolecule. For example, conditions such as buffer type, pH, electrolyte concentration and type, presence or absence of surfactant and concentration of any component, including of the nanoparticles, may be adjusted. Adjustment of the pH and ionic strength of the medium may occur in the presence or absence of the macromolecule. Typically adjustment of the pH and ionic strength of the medium, when in the presence of the nanoparticles, will occur in the presence also of the macromolecule so as to promote the binding between nanoparticles and the macromolecule, rather than binding only between nanoparticles that will cause aggregation and clumping.

The Examples herein indicate that binding of FibrinLite nanoparticles to a macromolecule may be achieved through the use of a pH near the pI of the macromolecule and a suitable concentration of the simple electrolyte sodium chloride (NaCl), which is effective in inducing avid binding of the nanoparticles to the macromolecule at concentrations of greater than about 1 mM NaCl. As will be appreciated, in view of the disclosure herein, appropriate conditions for inducing avid binding of nanoparticles to a macromolecule may be achieved using any one or more of a large variety of electrolytes. The inventors describe herein that a simple electrolyte concentration of greater than about 1 millimolar may be used to induce avid binding of nanoparticles to a macromolecule and thus, where the nanoparticles have a radioactive particulate core, to provide for the preparation of a radiolabelled macromolecule. Generally, the simple electrolyte concentration of the solution or medium for the contacting is expected to be in the range of about 1 millimolar to about 200 millimolar; typically, about 10 millimolar to about 175 millimolar; about 20 millimolar to about 150 millimolar; about 50 millimolar to about 150 millimolar. More typically the electrolyte concentration of the solution is expected to be in the range of about 1 millimolar to about 200 millimolar; typically from about 10 millimolar to about 175 millimolar; from about 20 millimolar to about 150 millimolar; from about 40 millimolar to about 150 millimolar; from about 50 millimolar to about 150 millimolar; from about 75 millimolar to about 150 millimolar; from about 90 millimolar to about 150 millimolar; from about 100 millimolar to about 150 millimolar; about 150 millimolar. A person of skill in the art will understand that the ionic strength of an electrolyte solution or medium for the contacting step of the present invention may be achieved by, for example, using NaCl wherein a suitable ionic strength may be achieved with an NaCl concentration of about 150 mM or, for example, a $MgSO_4$ concentration of less than about 75 mM. A person of skill in the art will also understand that a suitable ionic strength of an electrolyte solution may be achieved by use of a number of different ionic species, for example a mixture of NaCl and $MgSO_4$. Furthermore a person of skill in the art will understand the ionic strength may be achieved by use of at least one ionic species and at least one non-ionic species such as an osmolyte or high molecular weight polymer such as polyethylene glycol. For example, where the effective concentration of water is reduced, the concentration of electrolyte may need to be increased, for example at about 250 mM.

Any suitable ionic species may be used in the methods of the invention. For example, the ionic species may be selected from the group comprising salts of Na, Ni, Al, Ru, Pt, Os, Ir, Fe, Se, Sn, K, Te, Mn, Mo, V, Mg, Zn, Ca, Cu, Co. For medical or veterinary use in living subjects the ionic species will typically be limited to those that are non-toxic at the effective concentrations, e.g. Na, K, Ca. The skilled addressee will understand that, in the absence of any other relevant changes to a given set of reaction conditions (for example in a contacting step), K used instead of Na would typically be used at the same concentration as Na, whilst Ca used instead of Na would typically be used at half the concentration as Na.

The buffer used in the contacting step may be of any suitable pH. As described herein the pH of the aqueous medium is typically selected to be suitable for promoting short-range attractive forces between the nanoparticles and the macromolecule by suppressing repulsive electrostatic forces. The pH of the buffer will typically be selected on the basis of the macromolecule(s) to be utilised in the contacting. Preferably the buffer will be in the range from about pH 3 to about pH 10 or greater, from about pH 3 to about pH 8, from about pH 3.5 to about pH 8.5, from about pH 4 to about pH 8, from about pH 4.5 to about pH 7.5, from about pH 5 to about pH 7. More preferably the pH of the contacting step, such as the pH of the aqueous medium, will be near to the pI of the macromolecule to be utilised in the contacting, such as a polypeptide. More preferably still, the pH of the contacting step will be substantially at the pI of the macromolecule to be utilised in the contacting. As described herein the desired and optimal pH can be determined by the skilled addressee taking into account other reaction conditions, such as the electrolyte(s) type and concentration and the macromolecule(s).

The contacting may comprise modification of the conditions during the course of the contacting, such as an increase or decrease in the temperature of incubation during the contacting, or an increase or decrease of agitation of the medium or mixing during the contacting.

The methods of the invention are applicable to radiolabelling of any macromolecule. To illustrate the general applicability of the methods described herein, the Examples herein demonstrate high avidity binding of the nanoparticles to proteins having a low pI (albumin) and proteins having a high pI (protamine) as well as to polyclonal and monoclonal antibodies. On the basis of the description presented herein it will be apparent that the methods of the invention are applicable to radiolabelling of any macromolecule that presents in at least part of its surface a hydrophobic area (preferably the majority of the surface) under the conditions used for contacting with FibrinLite. It is also desirable that the macromolecule has a pI at which the macromolecule either maintains its biological activity or can regain its biological activity after return to near neutral pH.

The macromolecule may be presented to the FibrinLite nanoparticles in the contacting step in any suitable form such as free, for example as a solution, in an attached form as a coating or ligand on a surface of e.g. a metal, a synthetic polymer, or in an integrated form. To illustrate, a macromolecule in an "attached" form may also include the situation where the macromolecule is bound to a carrier, device or implant, such as a catheter or microparticle or microsphere, a nanoparticle, a liposome. The attachment may be of any suitable form including direct binding of the macromolecule to the carrier, device or implant or it may be indirect, such as through one or more intermediary molecules, such as on an ion-exchange resin, or adsorbed on a binding surface, or bonding agents. A macromolecule in an "integrated" form includes, for example, the situation where the macromolecule forms an integral part of a carrier, device or implant, such as a catheter, microparticle or microsphere. The coating or encapsulation may be partial or it may be complete. The macromolecule may also be displayed on the surface of a living cell or a liposome.

Accordingly, where the invention is utilised in the preparation of a radiolabelled medical device, the macromolecule may be contacted with, and hence labelled by, the carbon encapsulated nanoparticles (comprising a radioisotope or an inactive progenitor thereof) before being incorporated into or onto or otherwise being used for the preparation of a medical device, or the contacting may be after the macromolecule has been incorporated into or onto or otherwise been used for the preparation of a medical device, such that a medical device or a precursor thereof is used in the contacting.

The macromolecule may be presented to the FibrinLite nanoparticles in the contacting step comprised in or on a catheter, a fibre, a rod or filament, a membrane, a wafer, a mesh or gauze, a porous sponge, a tube or stent, a bead or capsule or microparticles in the form of microbeads of known dimensions, a nanoparticle, a liposome.

The radiolabelled macromolecule (or the macromolecule 'labelled' with an inactive progenitor of a radioisotope) may be used with or without one or more additional process steps. Where an additional step is implemented it may be simultaneously with the contacting or it may be subsequent to the contacting or, where multiple additional steps are implemented they may be a combination of additional steps simultaneously with the contacting and subsequent to the contacting. Where an additional step is implemented subsequent to the contacting, it may be in the presence of the same or a different media to that which was implemented for the contacting.

The radiolabelled macromolecule (or the macromolecule 'labelled' with an inactive progenitor of a radioisotope) may be subjected to one or more purification steps subsequent to the contacting. This may comprise separating radiolabelled macromolecule from unlabelled macromolecule and/or from free nanoparticle composite. In a typical reaction the contacting may result in satisfactory binding of nanoparticles to a macromolecule to provide radiolabelled macromolecule, whilst retaining in the aqueous media of the contacting step unreacted components, typically a proportion of nanoparticles composite which have not become attached to macromolecule. Removal of unreacted components may be desirable, for example in circumstances where free nanoparticles composite would be detrimental, such as blood transport to non-target organs. Removal of unbound macromolecule is desirable in the case where it will otherwise compete with the labeled macromolecule for specific binding sites, such as cell receptors or antigen sites, and thereby diminish the imaging capability or therapeutic capability of the labeled macromolecule. The removal of unreacted components may be partial, substantially complete or complete. In this context "partial" removal will be understood to include removal of any amount of one or more unreacted or undesired components, more typically removal of up to about 80%, 90% or 95% of one or more unreacted or undesired components and "complete" removal will be understood to be removal of greater than about 95% of one or more unreacted or undesired components. Typically removal of at least 95% of unreacted or undesired components is preferred, more preferably removal of greater than about 96%, 97%, 98%, or 99% of unreacted or undesired components.

Hence it will be understood that reference to "purification" in this context is intended to mean any degree of purification, whereby the radiolabelled macromolecule (or macromolecule 'labelled' with an inactive progenitor of a radioisotope) after a "purification" step contains less impurities, such as unreacted or undesired components of the contacting, compared to before the purification step.

Any method capable of separating radiolabelled macromolecule (or macromolecule 'labelled' with an inactive progenitor of a radioisotope) from unreacted or undesired components, such as unbound radioactive nanoparticles, may be used in a purification step. For example, the method may comprise washing one or more undesired components away from the radiolabelled macromolecule, or may comprise extracting the radiolabelled macromolecule away from the one or more undesired components, or may comprise a combination of such steps.

The radiolabelled macromolecule may be incorporated or integrated into or onto an entity, such as a biological or non-biological entity, for example a carrier, device or implant, such as a catheter or microparticle. Typically, the radiolabelled macromolecule to be incorporated or integrated into or onto is free in solution, suspension or dispersion. The radiolabelled macromolecule may be caused to be attached to an entity, such as a biological or non-biological entity, for example a carrier, device or implant, such as a catheter or microparticle. The attachment may be by any suitable method compatible with partial or complete retention of the radiolabel, including direct and indirect binding or attachment. Where a biological activity of a radiolabelled macromolecule is desired to be retained, the attachment may be any suitable method compatible with partial or complete retention of a biological activity of the macromolecule. The radiolabelled macromolecule may be used for coating or encapsulating of an entity such as a carrier, device or implant. The coating or encapsulation may be partial or it may be complete.

Medical devices, such as implantable devices such as vascular grafts and stents, may include additional modifications such as are known in the art. For example, the devices may include a bio-active such as a bio-active coating, having anti-thrombogenic and/or anti-infective properties such as by inclusion of anti-thrombogenic agents, antibiotics, antibacterial agents or antiviral agents. The preparation of implantable devices having bio-active coatings is known in the art and is described, for example in U.S. Pat. No. 6,803,069 to Patnaik et al and entitled "Method for imparting a bio-active coating modified", the entire contents of which are herein incorporated by reference.

Radiolabelling Polypeptides

The present invention provides methods for the radiolabelling of macromolecules, in particular biological macromolecules. The macromolecules include polypeptides. It will be understood that the term "polypeptide" as used herein means any polymer of amino acids joined by peptide bonds. The "polypeptide" may be of any length including, without limitation, molecules of less than about 50 amino acids and molecules of more than about 50 amino acids. Accordingly, as used herein the term "polypeptide" includes polymers of amino acids that may alternatively also be referred to as "peptides", such as molecules constituting of approximately 10 to 50 amino acids. The amino acids may include those occurring in nature as well as those synthesized in the laboratory which do not occur naturally, for example the D stereoisomers of the natural L forms occurring in nature. The polypeptides may be linear, branched or cyclized forms of naturally occurring peptides. For the sake of clarity, i.e. it is noted that the term "polypeptide" also includes proteins, including full length proteins, as well as immunogenic fragments of proteins, truncated and partial sequences, biologically active and inactive analogues and variants of proteins and precursor forms of proteins. The macromolecules may be polycations, such as polylysine, including poly-D-lysine, and protamine.

In one embodiment the poly-lysine is of molecular weight of about 1 kd to about 5 kD or from about 5 kd to about 15 kd, or from about 15 kd to about 30 kd, or from about 30 kd to about 40 kd, or from about 40 kd to about 50 kd, or from about 50 kd to about 60 kd, or from about 60 kd to about 70 kd, or from about 70 kd to about 80 kd, or from about 80 kd to about 90 kd, or from about 90 kd to about 100 kd. The polypeptides of the invention include naturally occurring polypeptides, whether isolated or derived from a naturally occurring source, such as physically extracted, purified or isolated from an organism, or generated in any manner such as, for example, chemical synthesis or recombinant production or cell-free synthesis in vitro.

The complexes of nanoparticles with surface bound polypeptides of the invention may be used as probe or detector species useful for detection or measurement of any ligand that has a specific interaction with the surface bound polypeptide. The polypeptide may be selected from a diverse range of molecules, such as the following non-limiting examples.

The macromolecules include polypeptides containing specific binding sites for an extracellular or intracellular protein, for the sub-units or monomer chains of a multimeric protein, for a cell-surface receptor, or for a cell-surface marker antigen such as an immunological marker or tumour diagnostic or prognostic marker. Binding of the polypeptide to a cell-surface receptor may also have biological functionality, such as induction of an anti-proliferative effect on the affected cells, or induction of apoptosis. Internalisation of the labelled probe by living cells in vitro may enable subsequent in vivo imaging of the biodistribution or tissue or organ localisation of the cells following their introduction into a living subject.

The macromolecules include antibodies or fragments of immunoglobulins that are reactive with an extracellular or intracellular protein, with the sub-units or monomer chains of a multimeric protein, with a cell-surface receptor, or with a cell-surface marker antigen such as an immunological marker or tumour diagnostic or prognostic marker. Internalisation of the labelled probe by living cells in vitro may enable subsequent in vivo imaging of the biodistribution of the cells following their introduction into a living subject.

In accordance with the present invention an IgG fraction of an animal or human antisera can be bound to the surface of nanoparticles, such as FibrinLite nanoparticles, using the methods described herein, and the resulting labelled probe may be used for example to detect or measure in a tissue sample extract or a body fluid sample the corresponding antigen specifically reactive with said immune IgG, using any of the known radiometric methods of immunoassay. The reactive antigen may have medical significance e.g. as a tumour marker in a cancer patient, in which case immunoassay of the sample may yield information of value to diagnosis, prognosis or management of therapy.

The ligand of interest may be accessible to the labelled probe after injection or regional delivery (e.g. by an arterial catheter) of the labelled probe in a living subject. The signal from the labelled probe may then be used for external imaging by methods known in the art such as single photon computed tomography (SPECT) or positron emission tomography (PET). The location and local concentration of the ligand of interest may thus be determined in vivo. Imaging by any modality known in the art may then reveal the presence or overabundance of the ligand at a tissue or organ site that may be due to a pathological lesion, such as a tumour.

The external imaging of the probe localization in the living body of humans and animals may then have diagnostic, prognostic or therapeutic value, such as in the assessment and treatment scheduling of a cancer patient.

In one embodiment the ligand of interest may be present in the biological sample or living body as a pharmaceutical, a diagnostic, a therapeutic substance, an infectious agent or a foreign substance, and its detection and measurement by the use of a labelled probe together with any of the methods herein may give clinically significant data about a patient's condition or response to a specific treatment.

In another embodiment a local abundance of a ligand of interest in the body may be a measure of the patient's response to a pharmaceutical administered as a therapeutic e.g. a cytotoxic drug, or a scheduled dose of a radiotherapy, e.g. a beam therapy, in which cases imaging of its location and abundance using a radiolabelled probe may provide an is early indication of e.g. response or lack of response of a tumour to chemotherapy or radiotherapy. This may be of value to the treating clinician in being able to make an early change if needed to a cancer patient's chemotherapy or radiotherapy schedule.

The FibrinLite nanoparticles described herein may carry the radioisotope as a detectable label that can be used for ex vivo radiometric assay or for in vivo imaging. In another embodiment the isotope may be chosen from those therapeutic radionuclides that are suitable for regional radiotherapy, e.g. $^{153}$Sm, $^{90}$Y, $^{192}$Ir, $^{103}$Pd, $^{111}$In, $^{166}$Ho. In this case the antibody used for coating FibrinLite (e.g. a monoclonal antibody) may be chosen so as to enable localization of a therapeutic dose of an isotope at a predetermined tissue or organ site by means of the antibody's specificity for a known ligand occurring in over-abundance at that site as a consequence of a disease state, e.g. a tumour marker in a cancer patient. The inventors have previously described the use of a diverse range of radioisotopes that may be incorporated in the nanoparticles, including gamma (e.g. Tc-99m), beta (e.g. Y-90), alpha (e.g. Bi-213) or positron (e.g. Cu-64) emitters. Some of these isotopes are ideally suited for imaging applications (e.g. SPECT using Tc-99m or Ga-67; PET using Cu-64, Ga-68, or Zr-89). Some of these isotopes are suitable for targeted radiotherapy as described above, and in fact are known in the art for use in ablation of certain types of tumours, e.g. Y-90 is used for regional ablation of liver metastases of colorectal cancer. In one embodiment the nanoparticle composite with bound protein may be separated from any excess unbound protein by any of several methods known in the art, such as size exclusion chromatography (molecular sieving) or centrifugation. However it should be noted that the solution of the polypeptide, protein or antibody does not have to be of so high a concentration as to saturate the surface of the nanoparticles. Instead, a sub-saturating concentration can be used, and a passive protein can be used to complete surface saturation and thus preserve specificity of the labelled probe. For example, if the nanoparticles are used to label a monoclonal antibody that has specificity for a tumour marker, and the available amount of the antibody is limiting, the surface saturation of the nanoparticles may be completed with non-immune gamma-globulin, or with other commercial blocking agents known to those skilled in immunoassay techniques. This will prevent the FibrinLite particles binding to irrelevant proteins or plastic surfaces in an immunoassay.

In one embodiment where the nanoparticle composites may be used for labelling probes that will be used in vivo for imaging purposes, it should be noted that intravenously injected uncoated, the nanoparticle composites are almost completely removed from the circulation within 20 minutes by the reticuloendothelial system, i.e. phagocytic cells such as the Kupffer cells of the liver. Therefore for in vivo imaging it may sometimes be desirable to use the nanoparticle composite preparations with special coatings designed to prolong the presence of the nanoparticle composite-labelled probe in the circulation and thus allow more time for binding of the probe to a specific target. In such cases the coating may be selected to suit the desired rate of clearance from the circulatory system, and to complement the probe protein on the nanoparticle surface. For this purpose the coating may be selected from those molecules known to extend circulation persistence, such as polyethylene glycol (PEG), or an antagonist of the receptors used as scavengers by the liver's reticuloendothelial system.

The surface of the nanoparticle composites may also be coated with purified plasma proteins prior to use in vivo, in order to reduce binding of reactive blood components in vivo, such as the complement system. Examples of plasma proteins that could be used include the classical adhesion proteins, such as vitronectin and fibronectin. Direct coating of particles with these proteins may also be used to enable conjugation of particles with other specific probe proteins, via cross-linking agents known to those skilled in protein chemistry. This may be desirable where direct binding of the probe protein to the FibrinLite particles is found to reduce avidity for the probe's specific ligand. This concept could be extended to multi-layer composites on the particle surface also for the purpose of increasing the surface density of interaction sites displayed, or to increase the physical particle size, or to facilitate multi-site interactions with cell-surface receptors, even of different receptor classes or specificities.

Methods for Coating of Fibrinlite Nanoparticle Composites with Proteins and Antibodies.

The nanoparticle composites of carbon encapsulated radionuclides may be prepared according to PCT/AU2006/000554. A neutral or slightly acid pH, stable aqueous dispersion of nanoparticles comprising carbon-encapsulated radionuclide (e.g. Tc-99m) can be produced. The dispersion of nanoparticles may also contain a very low (e.g., 10 micromolar) concentration of an anionic surfactant, sodium deoxycholate, which is compatible with and may be injected into, the blood circulation of a living subject (see FIGS. 5 and 6 herein). These particles can each carry tens of thousands or more of isotope atoms as the labelling source, so that very high levels of specific activity can readily be obtained that are well above those obtainable with traditional labelling methods. For nanoparticle composites with Tc-99m as the model encapsulated radioisotope, a typical preparation of nanoparticles can readily be made so as to contain between 1 and 30 mCi in 2 mL of aqueous suspension, as desired. From vapour phase characterization of the particles using scanning mobility particle sizing (SMPS) techniques, it can be shown that this suspension contains approximately 50 µg of nanoparticle material, so that the specific activity can be made as high as 600 mCi/mg, or over 22 GBq/mg.

The carbon encapsulation process wraps the metallic isotope in a carbon cage, so that it becomes physically isolated from contact with its external environment, an especially valuable property for the particles when they are to be used in vivo. The potential for leaching and bio-uptake of the radioactive metal ions in vivo is virtually non-existent. Only the carbon exterior of the nanoparticle composite is exposed to the biological environment in vivo. Because the carbon is in a graphitic form, it has natural adsorbent properties, and this can be used as the basis for physico-adsorption to selected polypeptides. It is first required however to determine appropriate conditions that will favour attachment of polypeptides, and the following studies and examples illustrate how these conditions can be determined.

The FibrinLite nanoparticle composites are capable of high avidity binding via hydrophobic or dispersion interactions, involving their graphitic surface. In order for the graphitic surface to form hydrophobic interactions with macromolecules, such as polypeptides, the polypeptide must be able to approach the graphite surface at very close range, thus in turn necessitating that repulsive electrostatic forces are suppressed. The inventors show that this condition can be met when the polypeptide is presented to the nanoparticle preparations with minimum net surface charge, either by adjusting the pH to near the isoelectric point of the polypeptide, or by shielding the charge of the polypeptide with an appropriate concentration of electrolyte counterions. Empirical binding experiments may be used to establish appropriate binding conditions. While the following studies and examples centre on the FibrinLite nanoparticle composite interaction with immunoglobulins, it will be understood that the same methods can be applied to determine the appropriate conditions for interaction of the FibrinLite nanoparticle composites with virtually any polypeptide.

Most antibodies in biomedical research, medical diagnostic and therapeutic use consist of plasma gamma-globulins belonging to the IgG class of immunoglobulins. While most globular proteins in plasma have an isoelectric point between pH 4.5 and pH is 6.5, IgG comprises a diverse range of individual proteins with isoelectric points mostly between 5.5 and 8.0. Nevertheless it can be assumed that while, for example, albumin is closer to its isoelectric point at say pH 3.5 than most plasma IgG, at pH 6.0 most IgG's will be closer to their iso-electric point than albumin. Thus IgG's and hence most antibodies will have least charge and should be most able to interact with FibrinLite at or near neutral pH.

The inventors describe herein methods by which avid binding of macromolecules and carbon encapsulated nanoparticle composites can be induced. The description herein is illustrated by reference to preferred embodiments and examples. On the basis of the description herein the skilled addressee will appreciate that where alternatives are used appropriate conditions may be determined empirically, such alternatives including the radioactive isotope or inactive progenitor thereof, the macromolecule(s), the electrolyte and the pH.

Pharmaceutical and/or Therapeutic Formulations

The present invention also provides pharmaceutical and therapeutic compositions of radiolabelled macromolecules, such as radiolabelled biological macromolecules, where the macromolecule is in association with a carbon encapsulated nanoparticle composite having a radioactive particulate core (FibrinLite). Typically, for medical use, salts of the compounds of the present invention will be pharmaceutically acceptable salts; although other salts may be used in the preparation of the inventive compounds or of the pharmaceutically acceptable salt thereof. By pharmaceutically acceptable salt it is meant those salts which, within the scope of sound medical judgement, are suitable for use in contact with the tissues of humans and lower animals without undue toxicity, irritation, allergic response and the like, and are commensurate with a reasonable benefit/risk ratio. Pharmaceutically acceptable salts are well known in the art.

S. M. Berge et al. describe pharmaceutically acceptable salts in detail in *J. Pharmaceutical Sciences,* 1977, 66:1-19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphorsulfonate, citrate, digluconate, cyclopentanepropionate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium potassium, calcium, magnesium, and the like, as well as non-toxic ammonium, quaternary ammonium, and amine cations, including, but not limited to ammonium, tetramethylammonium, tetraethylammonium, methylamine, dimethylamine, trimethylamine, triethylamine, ethylamine, triethanolamine and the like.

Convenient modes of administration include injection (subcutaneous, intravenous, etc.), oral administration, inhalation, transdermal application, topical creams or gels or powders, or rectal administration. In one embodiment, the mode of administration is parenteral. In another embodiment, the mode of administration is oral. Depending on the route of administration, the formulation and/or compound may be coated with a material to protect the compound from the action of enzymes, acids and other natural conditions which may inactivate the therapeutic activity of the compound. The compound also may be administered parenterally or intraperitoneally.

Dispersions of compounds according to the invention may also be prepared in glycerol, liquid polyethylene glycols, and mixtures thereof and in oils. Under ordinary conditions of storage and use, pharmaceutical preparations may contain a preservative to prevent the growth of microorganisms.

Pharmaceutical compositions suitable for injection include sterile aqueous solutions (where water soluble) or dispersions and sterile powders for the extemporaneous preparation of sterile injectable solutions or dispersions. Ideally, the composition is stable under the conditions of manufacture and storage and may include a preservative to stabilise the composition against the contaminating action of microorganisms such as bacteria and fungi.

The compound(s) of the invention may be administered orally, for example, with an inert diluent or an assimilable edible carrier. The compound(s) and other ingredients may also be enclosed in a hard or soft shell gelatin capsule, compressed into tablets, or incorporated directly into an individual's diet. For oral therapeutic administration, the compound(s) may be incorporated with excipients and used in the form of ingestible tablets, buccal tablets, troches, capsules, elixirs, suspensions, syrups, wafers, and the like. Suitably, such compositions and preparations may contain at least 1% by weight of active compound. The percentage of the compound(s) of the invention, typically a radiolabelled polypeptide in pharmaceutical compositions and preparations may, of course, be varied and, for example, may conveniently range from about 2% to about 90%, about 5% to about 80%, about 10% to about 75%, about 15% to about 65%; about 20% to about 60%, about 25% to about 50%, about 30% to about 45%, or about 35% to about 45%, of the weight of the dosage unit. The amount of compound in therapeutically useful compositions is such that a suitable dosage will be obtained.

The language "pharmaceutically acceptable carrier" is intended to include solvents, dispersion media, coatings, antibacterial and anti-fungal agents, isotonic and absorption delaying agents, and the like. The use of such media and agents for pharmaceutically active substances is well known in the art. Except insofar as any conventional media or agent is incompatible with the compound, use thereof in the therapeutic compositions and methods of treatment and prophylaxis is contemplated. Supplementary active compounds may also be incorporated into the compositions according to the present invention. It is especially advantageous to formulate parenteral compositions in dosage unit form for ease of administration and uniformity of dosage. "Dosage unit form" as used herein refers to physically discrete units suited as unitary dosages for the individual to be treated; each unit containing a predetermined quantity of compound(s) is calculated to produce the desired therapeutic effect in association with the required pharmaceutical carrier. The compound(s) may be formulated for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

In one embodiment, the carrier is an orally administrable carrier.

Another form of a pharmaceutical composition is a dosage form formulated as enterically coated granules, tablets or capsules suitable for oral administration.

Also included in the scope of this invention are delayed release formulations.

Compounds according to the invention also may be administered in the form of a "prodrug". A prodrug is an inactive form of a compound which is transformed in vivo to the active form. Suitable prodrugs include esters, phosphonate esters etc, of the active form of the compound.

In one embodiment, the compound of the invention may be administered by injection. In the case of injectable solutions, the carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by including various anti-bacterial and/or anti-fungal agents. Suitable agents are well known to those skilled in the art and include, for example, parabens, chlorobutanol, phenol, benzyl alcohol, ascorbic acid, thimerosal, and the like. In many cases, it may be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminium monostearate and gelatin.

Sterile injectable solutions can be prepared by incorporating the analogue in the required amount in an appropriate solvent with one or a combination of ingredients enumerated above, as required, followed by filtered sterilisation. Generally, dispersions are prepared by incorporating the analogue into a sterile vehicle which contains a basic dispersion medium and the required other ingredients from those enumerated above.

Tablets, troches, pills, capsules and the like can also contain the following: a binder such as gum gragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavouring agent such as peppermint, oil of wintergreen, or cherry flavouring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the analogue, sucrose as a sweetening agent, methyl and propylparabens as preservatives, a dye and flavouring such as cherry or orange flavour. Of course, any Material used in preparing any dosage unit form should be pharmaceutically pure and substantially non-toxic in the amounts employed. In addition, the analogue can be incorporated into sustained-release preparations and formulations.

Preferably, the pharmaceutical composition may further include a suitable buffer to minimise acid hydrolysis. Suitable buffer agent agents are well known to those skilled in the art and include, but are not limited to, phosphates, citrates, carbonates and mixtures thereof.

Single or multiple administrations of the compounds and/or pharmaceutical compositions according to the invention may be carried out. One skilled in the art would be able, by routine experimentation, to determine effective, non-toxic dosage levels of the compound and/or composition of the invention and an administration pattern which would be suitable for treating the diseases and/or infections to which the compounds and compositions are applicable.

Further, it will be apparent to one of ordinary skill in the art that the optimal course of treatment, such as the number of doses of the compound or composition of the invention given per day for a defined number of days, can be ascertained using convention course of treatment determination tests.

Generally, an effective dosage per 24 hours may be in the range of about 0.0001 mg to about 1000 mg per kg body weight; for example, about 0.001 mg to about 750 mg per kg body weight; about 0.01 mg to about 500 mg per kg body weight; about 0.1 mg to about 500 mg per kg body weight; about 0.1 mg to about 250 mg per kg body weight; or about 1.0 mg to about 250 mg per kg body weight. More suitably, an effective dosage per 24 hours may be in the range of about 1.0 mg to about 200 mg per kg body weight; about 1.0 mg to about 100 mg per kg body weight; about 1.0 mg to about 50 mg per kg body weight; about 1.0 mg to about 25 mg per kg body weight; about 5.0 mg to about 50 mg per kg body weight; about 5.0 mg to about 20 mg per kg body weight; or about 5.0 mg to about 15 mg per kg body weight.

Alternatively, an effective dosage may be up to about 500 mg/m². For example, generally, an effective dosage is expected to be in the range of about 25 to about 500 mg/m², about 25 to about 350 mg/m², about 25 to about 300 mg/m², about 25 to about 250 mg/m², about 50 to about 250 mg/m², and about 75 to about 150 mg/m².

In another embodiment, a compound of the invention may be administered in an amount in the range from about 100 to about 1000 mg per day, for example, about 200 mg to about 750 mg per day, about 250 to about 500 mg per day, about 250 to about 300 mg per day, or about 270 mg to about 280 mg per day.

Compounds in accordance with the present invention may be administered as part of a therapeutic regimen with other drugs. It may be desirable to administer a combination of active compounds, for example, for the purpose of treating a particular disease or condition. Accordingly, it is within the scope of the present invention that two or more pharmaceutical compositions, at least one of which contains a compound of the invention, may be combined in the form of a kit suitable for co-administration of the compositions.

The invention will now be described in more detail, by way of illustration only, with respect to the following examples. The examples are intended to serve to illustrate this invention and should not be construed as limiting the generality of the disclosure of the description throughout this specification.

EXAMPLES

Example 1

The binding of FibrinLite to gamma-globulins at different pH conditions was studied in this series of experiments, as follows. Binding tests were made after saturation coating of microwells with rabbit immunoglobulins in a 96 well microplate that enabled individual measurement of radioactivity of separated wells after binding and multiple washing steps. Citrate buffer (500 μM) was used at both pH 3.5 and pH 6.0 to enable direct comparison of the effect of pH on binding and at both very low and physiological electrolyte concentrations, detailed as follows.

Influence of pH on FibrinLite Binding to Rabbit Immunoglobulin Coated Microwells Polystyrene microwells (Nunc-Immuno LockWell™ modules) were first saturation coated with rabbit immunoglobulin (IgG, Sigma I5006). The wells were coated with IgG solution at 500 μg/mL (100 μL/well) for 3 h at 37° C. with agitation. Diluted (1:10) Tc-99m FibrinLite was contacted with the coated polystyrene microwells under various buffer conditions, set out as conditions (i) to (viii), namely:

(i) 500 μM sodium citrate pH 3.5 (low electrolyte conditions);
(ii) 500 μM sodium citrate pH 3.5 plus 10 μM sodium deoxycholate (DOC);
(iii) 500 μM sodium citrate pH 3.5 plus 150 mM NaCl;
(iv) 500 μM sodium citrate pH 3.5 plus 10 μM sodium deoxycholate plus 150 mM NaCl;
(v) 500 μM sodium citrate pH 6.0 (low electrolyte conditions);
(vi) 500 μM sodium citrate pH 6.0 plus 10 μM sodium deoxycholate (DOC);
(vii) 500 μM sodium citrate pH 3.5 plus 150 mM NaCl; and
(viii) 500 μM sodium citrate pH 6.0 plus 10 μM sodium deoxycholate plus 150 mM NaCl.

Binding was allowed for 20 minutes incubation at 37° C. with agitation and then the wells were rinsed five times with water before counting radioactivity in individually separated wells.

Figure 1A:
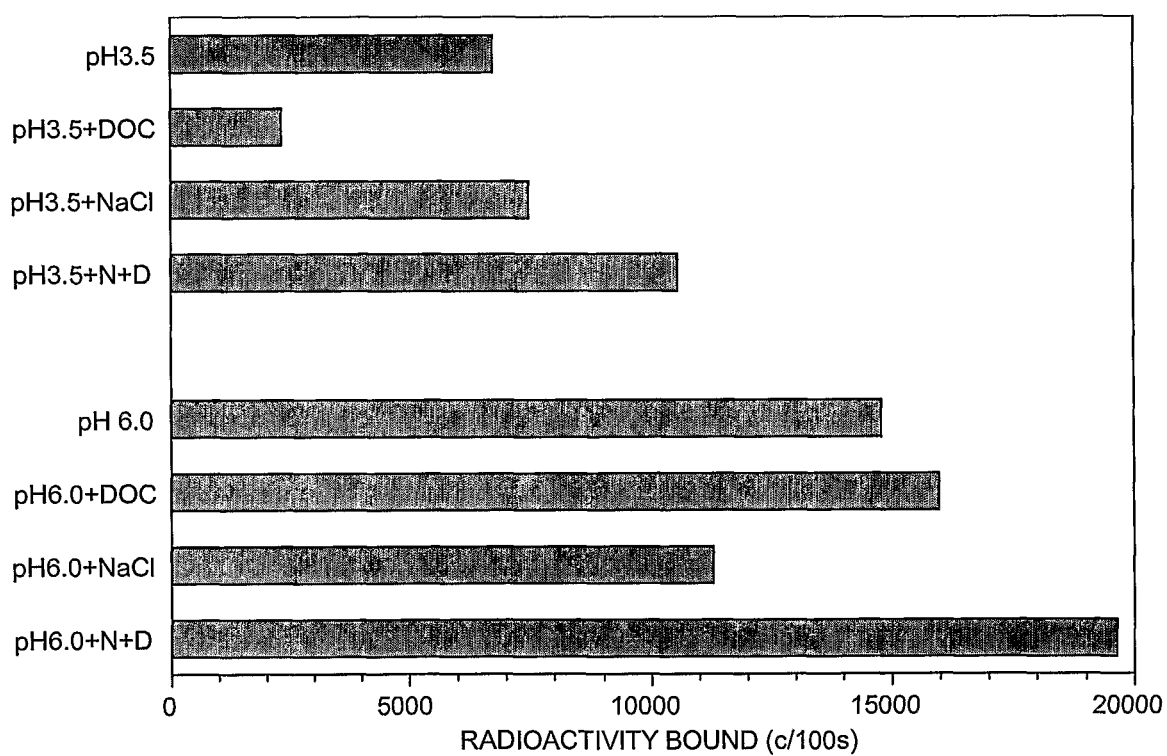
FIG. 1a: Influence of pH on FibrinLite binding to rabbit immunoglobulin coated microwells. Binding of a Tc-99m FibrinLite dilution (1:10; 100 µL) to rabbit immunoglobulin (Sigma I5006) coated polystyrene microwells (Nunc Lockwells™) under various conditions, as shown. 500 µM sodium citrate pH 3.5 ("pH 3.5"); 500 µM sodium citrate pH 3.5 plus 10 µM sodium deoxycholate ("pH 3.5 DOC"); 500 µM sodium citrate pH 3.5 plus 150 mM NaCl ("pH 3.5+NaCl"); 500 µM sodium citrate pH 3.5 plus 10 µM DOC plus 150 mM NaCl ("pH 3.5+N+D"); the annotations "pH 6.0", "pH 6.0+DOC", "pH 6.0+NaCl", and "pH 6.0+N+D" have corresponding meanings but at pH 6.0 rather than pH 3.5. The bars represent means of duplicate wells.

As shown in FIG. 1a, and contrary to the binding of FibrinLite to uncoated polystyrene microwells (data not shown), binding to IgG coated wells was stronger at pH 6.0 than at pH 3.5, and appreciable radiolabel density was obtainable without addition of electrolyte. In fact, unlike the binding of FibrinLite to uncoated polystyrene wells, binding to an IgG coating was not enhanced by addition of 150 mM sodium chloride. Once bound, the FibrinLite particles attached in the absence of electrolyte were also held with high avidity, as evidenced by the retention of radiolabel after multiple washes in the binding assay. Furthermore binding of particles to the IgG coating at pH 6.0 still occurred in the presence of 10 μM sodium deoxycholate, an ionic surfactant, indicating a strong stable interaction without the need for electrolyte. By contrast, the lower binding obtained at pH 3.5 was significantly reduced by deoxycholate (FIG. 1a).

Figure 1B:
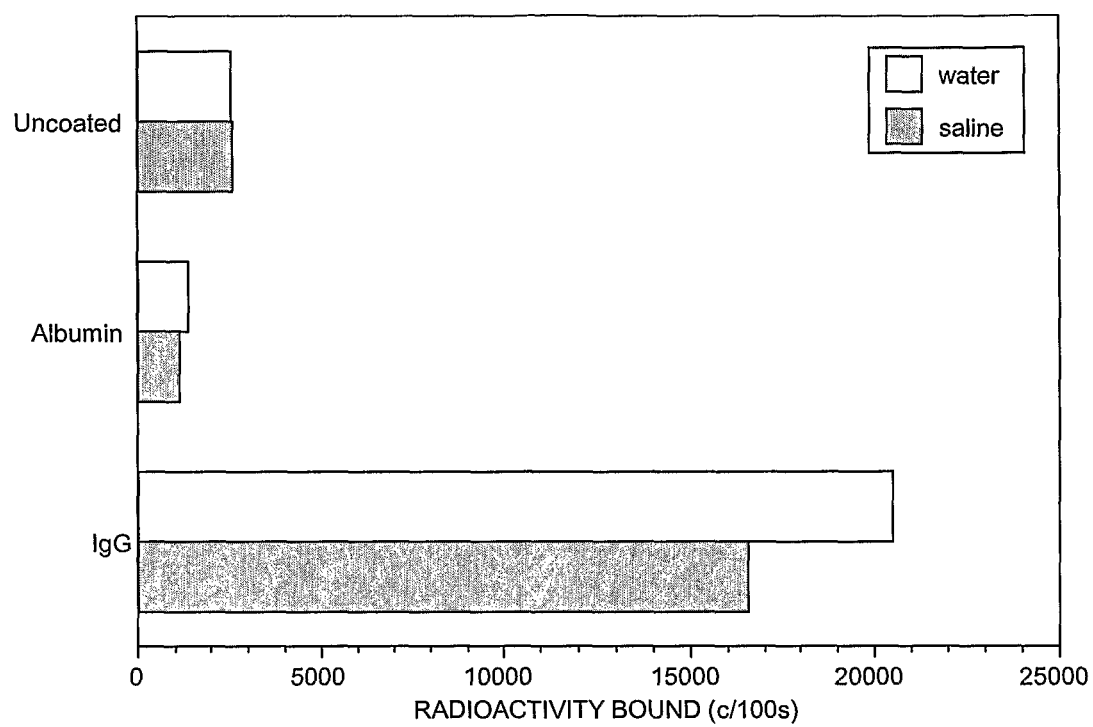
FIG. 1b: Binding of Tc-99m FibrinLite to microwells uncoated, after saturation coating with rabbit serum albumin (Sigma A0764), or after saturation coating with rabbit immunoglobulins (IgG; Sigma 15006). The bars represent means of duplicate wells.

In another experiment binding of a Tc-99m FibrinLite dilution (1:10; 100 μL) to polystyrene microwells (Nunc Lockwells™) previously coated with albumin or immunoglobulins was investigated. The microwells were coated by incubating with agitation for 3 hr at 37° C. with aliquots (100 μL/well) of rabbit serum albumin (Sigma A0764; 250 μg/mL) or rabbit immunoglobulins (IgG, Sigma I5006; 250 μg/mL). FibrinLite was diluted 1:10 into 0.5 mM trisodium citrate buffer pH 6.3, and aliquots (100 μL) of the dilution were dispensed on the coated and rinsed wells and allowed to bind for 20 min at 37° C. with agitation. After rinsing 5 times with either water or physiological saline (150 mM NaCl), the individual wells were detached and counted (FIG. 1b). The bars represent means of duplicate wells.

As shown in FIG. 1b, at very low electrolyte concentration (in this case 0.5 mM trisodium citrate buffer pH 6.3) and near neutral pH (6.3), immunoglobulin but not albumin can bind FibrinLite. Since albumin has a negative charge at neutral pH due to its low isoelectric point, while immunoglobulins have isoelectric points closer to neutral, these results are consistent with FibrinLite binding being dependent on attractive interactions that are favoured by near zero charge on the potential ligand. This type of interaction is also supported by the observation that the majority of the bound FibrinLite is not released by rinsing with saline compared to rinsing with water.

Example 2

FibrinLite Binding to Immunoglobulin: Polyclonal and Monoclonal

The rabbit immunoglobulins used in the experiments described in Example 6 above were prepared from normal non-immunised rabbits. The possibility was also tested that immunisation may significantly alter the average isoelectric point of the immunoglobulin population, and thus the binding to FibrinLite. Purified IgG from immunized rabbits was therefore tested, as follows.

Polystyrene microwells (Nunc-Immuno LockWell™ modules) were first saturation coated by incubating with agitation for 3 hr at 37° C. with aliquots (100 μL/well) of an immune preparation of rabbit immunoglobulins (R 389; American Diagnostica), or with one of two different murine monoclonal antibodies of IgG (Mab 3689 and Mab 3471; American Diagnostica). A Tc-99m FibrinLite dilution (1:10) was then added to uncoated and coated microwells, under low electrolyte conditions (500 μM sodium citrate at either pH 6 or pH 6.5).

Binding was allowed for 30 minutes incubation at 37° C. with agitation. The wells were then rinsed five times with water before counting radioactivity in the individual separated wells.

Figure 2:
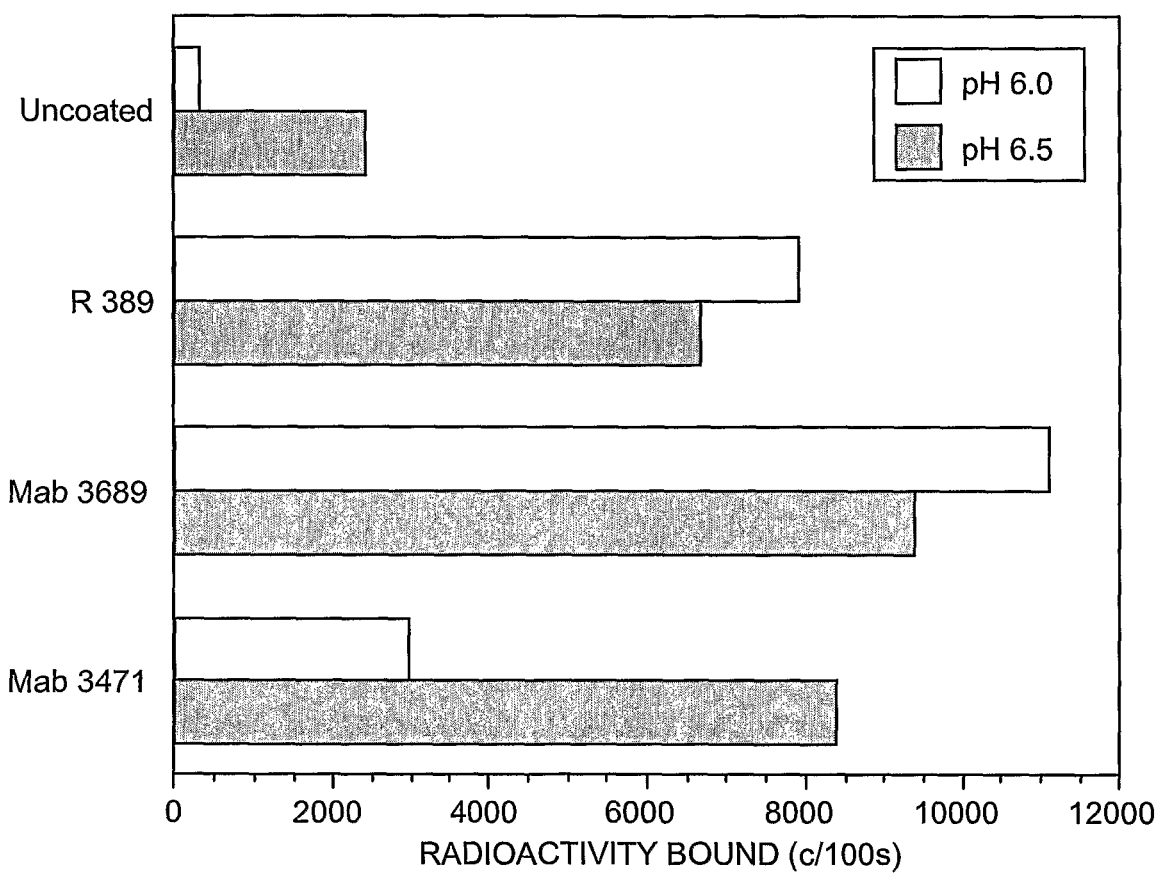
FIG. 2: Binding of Tc-99m FibrinLite to microwells uncoated, after saturation coating with an immune preparation of rabbit immunoglobulins (R 389; American Diagnostica), and after saturation coating with two different murine monoclonal antibodies of IgG (Mab 3689 and Mab 3471; American Diagnostica). The bars represent means of duplicate wells.

As shown in FIG. 2, strong and appreciable binding of FibrinLite was still obtained with the immune preparation of rabbit immunoglobulins at pH 6.0 and without addition of electrolyte.

The rabbit immunoglobulin preparations used above (e.g., R 389) represented the products of many different clones of immune cells, i.e. they were by nature polyclonal, and therefore were comprised of a population of many discrete IgG molecules, each likely to have different isoelectric points. By contrast, a monoclonal antibody represents the product of a single clone of cells and is comprised of only one immunoglobulin molecule, with its own characteristic isoelectric point. Therefore, while it is less likely that one binding condition can be used to obtain appreciable or optimal labelling of all monoclonal antibodies with FibrinLite, binding experiments of the type shown can determine suitable conditions for a given case.

This is illustrated in FIG. 2 using two different murine monoclonal antibodies. At pH 6.0 one monoclonal (Mab 3689; American Diagnostica) bound FibrinLite at relatively high levels but only relatively low level binding of FibrinLite to the other monoclonal (Mab 3471; American Diagnostica) was apparent. Increasing the pH to 6.5 was sufficient to enable a relatively high degree of binding in both cases (Mab 3689 and Mab 3471). Thus for monoclonal antibodies, each case should be treated separately and the conditions optimised with respect to pH (and if necessary electrolyte concentration) by using microwell binding assays, for example as described herein. The over-riding principle is to favour short-range attractive interactions between the FibrinLite nanoparticles and the antibody by reducing the nett charge on the antibody. This can be achieved by adjusting the pH as close as possible to the isoelectric point of the antibody.

Example 3

To better illustrate the general principle, a binding experiment was performed with two proteins that have widely different isoelectric points, namely serum albumin (low pI) and protamine (high pI). Polystyrene microwells were saturation coated with rabbit serum albumin or protamine. The wells were coated with each protein at 500 µg/mL in phosphate-buffered saline pH 7.2 (100 µL/well) for 3 h at 37° C. with agitation. After rinsing 5 times with water, a Tc-99m FibrinLite dilution (1:10) was added to the wells (100 µL/well) in low electrolyte conditions (500 µM sodium citrate) at either pH 3.5 or pH 6.5. Binding was allowed for 30 minutes incubation at 37° C. with agitation, and the wells were rinsed five times with water before counting radioactivity in the individual wells.

Figure 3:
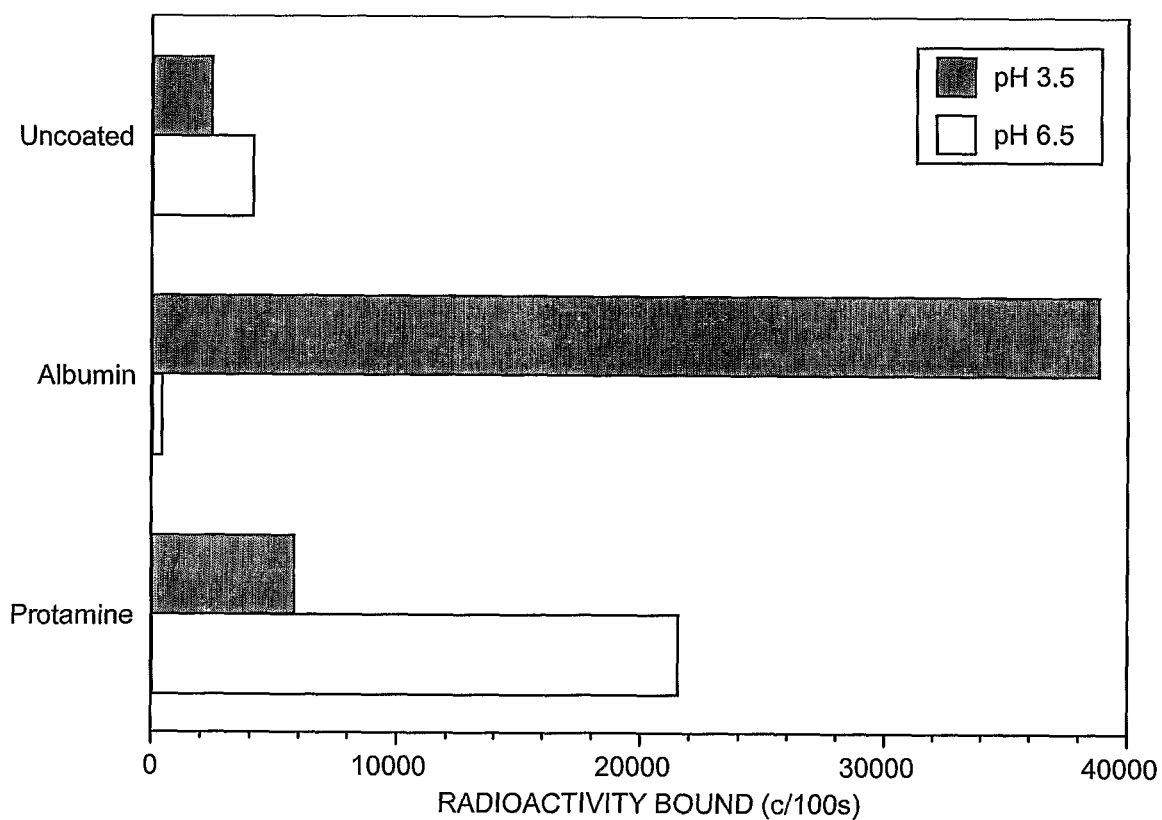
FIG. 3: Binding of Tc-99m FibrinLite to microwells uncoated, after saturation coating with rabbit serum albumin (Sigma A0764) or protamine sulphate (Sigma P4505), in 500 mM sodium citrate at pH 3.5 (shaded bars) or pH 6.5 (unshaded bars). The bars represent means of duplicate wells.

Binding results are shown for serum albumin, whose isoelectric point is at pH 4.4-5.1, and protamine, whose isoelectric point is at pH>10 (FIG. 3). Very high binding of FibrinLite to albumin was obtained at pH 3.5, close to albumin's isoelectric point, but at this pH only low binding of FibrinLite to protamine was obtained. On the contrary, appreciable binding of FibrinLite to protamine was obtained at pH 6.5, further towards protamine's isoelectric point, and at this pH insignificant binding to albumin was obtained. Thus, for any given protein stronger FibrinLite binding can be obtained using pH conditions close to that protein's isoelectric point.

Example 4

Electrolyte Induction of Fibrinlite Binding to Albumin

Figure 4:
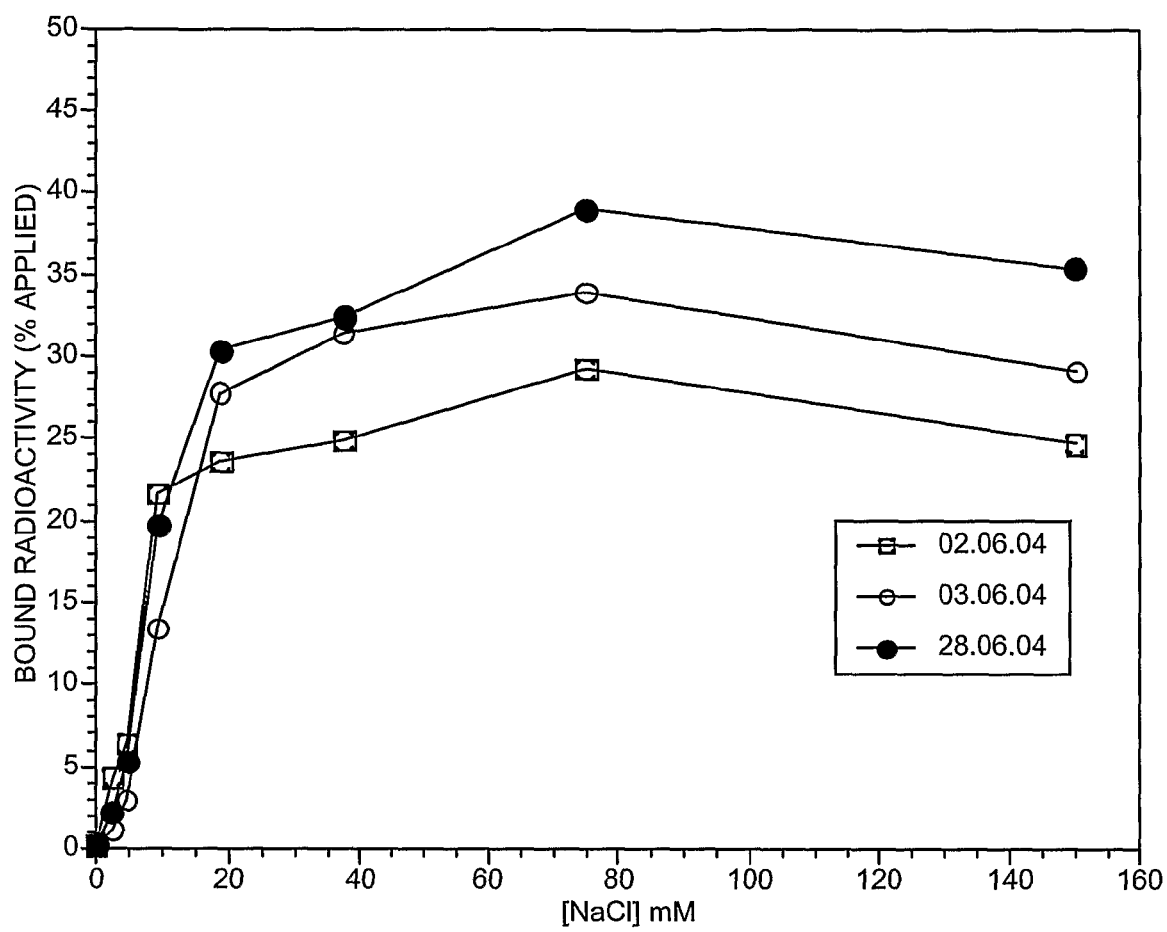
FIG. 4: Electrolyte induction of FibrinLite binding to Albumin

Electrolyte induced binding of a Tc-99m FibrinLite to polystyrene microwells (Nunc Lockwells™) previously coated with albumin. The wells were coated by incubation with agitation for 3 hr at 37° C. with 500 µg/mL rabbit serum albumin (100 µL/well; Sigma A0764) and rinsed 3 times with water. FibrinLite was diluted 1:10 into solutions of 0, 4.69, 9.38, 18.75, 37.5, 75, and 150 mM NaCl, and aliquots (100 µL) of the dilutions were dispensed on the coated and rinsed wells and allowed to bind for 30 min at 37° C. with agitation. After rinsing 4 times with water, the individual wells were detached and counted. Three independent experiments with three different preparations of FibrinLite were undertaken, as shown in FIG. 4.

As shown previously in FIGS. 1b and 3, FibrinLite shows only very weak binding to albumin-coated microwells at pH 6.5, but binds strongly at pH 3.5, i.e. close to albumin's isoelectric point where its attractive interactions predominate. However, as shown in FIG. 4, at near neutral pH where albumin is negatively charged, binding of FibrinLite can be induced by addition of sufficient electrolyte Example 5

Removal from the Circulation of IV Injected Uncoated FibrinLite

Tc-99m labelled FibrinLite (approx 1.9 mCi in 1.0 mL) was injected into an ear vein of an anaesthetised rabbit positioned under the detector head of a Siemens Diacam gamma camera. Acquisition of a sequence of images was started immediately upon injection. Each of the frames shown in FIG. 5 represents a 30 second interval thereafter. The rabbit's head is to the left of each frame. Radioisotope is seen to rapidly transit the heart and lungs, and accumulate in the liver and spleen. After just 4 minutes (frame 8) the large majority of injected radioactivity is localised to the liver and spleen.

Thus, intravenously injected uncoated FibrinLite nanoparticles are almost completely removed from the circulation within 20 minutes. This depletion is mediated by the reticuloendothelial system, i.e. phagocytic cells such as the Kupffer cells of the liver. For in vivo imaging it may sometimes be desirable to use the nanoparticle composite preparations with special coatings designed to prolong the presence of the nanoparticle composite-labelled probe in the circulation and thus allow more time for binding of the probe to a specific target. In such cases the coating may be especially selected to suit the desired rate of clearance from the circulatory system, and to complement the probe protein on the nanoparticle surface. For this purpose the coating may be selected from those molecules known to extend circulation persistence, such as polyethylene glycol (PEG), or an antagonist of the cellular receptors used as scavengers by the liver's reticuloendothelial system, such as polyinosinic acid.

Example 6

In Vivo Imaging Using Poly-Lysine Coated Fibrinlite

The surface of the nanoparticle composites may also be coated with selected agents that specifically redirect organ biodistribution of the nanoparticle composites in vivo. This may be desirable for imaging or therapy of disease lesions, e.g. tumours in the new destination organ.

An example is illustrated in FIG. 6, which shows specific imaging of rabbit lungs with Tc-99m FibrinLite that has been treated with a typical polycation, poly-D-lysine. Tc-99m labelled nanoparticle composites (approx 3.5 mCi in 1.0 mL) were treated for 1 hour with 3.0 μg/mL of poly-D-lysine (Sigma P4408; molecular weight 15-30 kd) in 0.5 mM Tris-acetate buffer pH 6.0 at room temperature. The mixture was then injected into an ear vein of an anaesthetised rabbit positioned under the detector head of a Siemens Diacam gamma camera. Acquisition of a sequence of images was started immediately upon injection and each of the frames shown in FIG. 6 represents a 30 second interval thereafter. The rabbit's head is to the right of each frame. Radioisotope is seen to rapidly accumulate almost exclusively in the lungs, and to stably persist there to the end of the acquisition sequence (4 min).

FIG. 6 shows that treating Tc-99m FibrinLite nanoparticles with poly-D-lysine is an effective method to produce specific accumulation of radiolabel in the blood vessel network of the lungs, thus enabling imaging of said network. The polymer of the non-naturally occurring D-stereoisomer of lysine was used in order to reduce the likelihood of proteinase degradation of the polymer in vivo, which is specific for the natural L-stereoisomer of lysine. Rabbits investigated using this method of lung imaging recovered uneventfully after the procedure, and some rabbits were repeat investigated three times each over a period of several weeks, when closely similar lung images were obtained on each occasion. Rabbits that had received multiple injections of this formulation of FibrinLite did not show any adverse effect and were normal by all appearances and behaviour. By this means it is proposed that the poly-D-lysine treated nanoparticle composites can be used to detect any pathological disturbance of the normal blood circulation in the lungs, resulting from either obstruction of flow (by e.g. an embolism), or from remodelling of the network (by e.g. tumour-induced angiogenesis). Thus poly-D-lysine treated Tc-99m FibrinLite is an illustrative and non-limiting example of a targeted imaging agent for lung diagnostics/prognostics. Equally however, the nanoparticle composites may be produced containing a therapeutic isotope, e.g. Y-90, instead of an imaging isotope, and after treatment with a suitable polycation may then be used for regional radiotherapy of primary or metastatic tumour(s) presenting in the lung.

Example 7

Effect of Poly-D-Lysine Molecular Weight on Fibrinlite Biodistribution

Tc-99m FibrinLite was pretreated for 1 h at 20° C. with poly-D-lysine of two different molecular weight ranges: A, MW 4-15 kd (6.0 μg/mL; Sigma P6403), and B, MW 30-70 kd, (1.5 μg/mL; Sigma P7886) in 0.5 mM Tris-acetate buffer pH 6. Each pretreated FibrinLite preparation (3.5 mCi) was injected into an ear vein of an anaesthetised rabbit and the biodistribution of the Tc-99m label was imaged under a Siemens Diacam gamma camera. Acquisition of a sequence of images was initiated immediately upon injection; each frame represents a 30 second interval. The rabbit's head is to the right of each frame.

This experiment shows that the lung imaging obtained with poly-D-lysine treated Tc-99m FibrinLite is dependent on the molecular size of the polycation (FIGS. 7A and 7B). Surprisingly, this property is not a simple function of polycation molecular size; while poly-D-lysine of molecular weight 15-30 kd was effective for specific lung imaging (see FIG. 6 above), neither the equivalent molar concentration of poly-D-lysine of molecular weight 4-15 kd nor the poly-D-lysine of molecular weight 30-70 kd were as effective. The 4-15 kd poly-D-lysine gave some lung specificity, but a significant proportion of label still appeared in the spleen (FIG. 7A). The 30-70 kd poly-D-lysine was clearly worse, with considerable label appearing in the liver, spleen and bone marrow (FIG. 7B), not dissimilar to untreated Tc-99m FibrinLite.

Thus it is shown that using the Tc-99m FibrinLite labelling method, different macromolecules can readily be assessed for their usefulness in targeting a given organ in vivo. This is conveniently achieved without resort to organic chemistry and using very low concentrations of the targeting molecule.

DISCUSSION

The examples herein demonstrate that high avidity labelling of macromolecules such as polypeptides can be achieved through suitable pH, and optionally electrolyte, conditions under which short range attractive forces predominate over repulsive electrostatic forces. The examples indicate that as the binding between FibrinLite and macromolecules involves attractive hydrophobic, ion correlation or dispersion interactions which are relatively insensitive to increased electrolyte concentrations, the binding can be utilized at physiological electrolyte concentrations. Using the methods described herein, FibrinLite nanoparticles are strongly retained in association with macromolecules, and the radiolabel will not dissociate under electrolyte conditions that may be encountered in vivo.

In the case of polypeptides, charged chemical groups (e.g. carboxylate or amino) are present on the polypeptide surface, and the nett charge of the polypeptide molecule is therefore a function of the pH of the polypeptide's environment. In this situation binding of FibrinLite to a polypeptide can be induced by adjusting the pH so that it is close to the pI of the polypeptide, where the nett charge is effectively zero. Binding is favoured by suppressing the repulsive electrostatic forces, so that short range attractive forces can predominate.

The foregoing describes preferred forms of the present invention. It is to be understood that the present invention should not be restricted to the particular embodiment(s) shown above. Modifications and variations, obvious to those skilled in the art can be made thereto without departing from the scope of the present invention.

The invention claimed is:

1. A method for detecting a disease or condition affecting blood circulation in a lung of a subject, the method comprising:

administering intravenously to said subject a complex comprising a macromolecule that is selective for lung tissue and a carbon encapsulated nanoparticle composite having a radioactive particulate core, wherein the macromolecule is poly-lysine having a molecular weight of about 15 to 30 kilodaltons and wherein the carbon encapsulated nanoparticle composite is a carbon encapsulated $^{99m}$Tc, $^{113m}$In, $^{111}$In, $^{198}$Au, $^{64}$Cu, $^{213}$Bi, $^{57}$Co, $^{51}$Cr, $^{165}$Dy, $^{169}$Er, $^{59}$Fe, $^{153}$Gd, $^{166}$Ho, $^{177}$Lu, $^{103}$Pd, $^{81}$Rb, $^{82}$Rb, $^{186}$Re, $^{188}$Re, $^{75}$Se, $^{153}$Sm, $^{117m}$Sn, $^{89}$Sr, $^{201}$Tl, $^{90}$Y, or $^{169}$Yb nanoparticle having a diameter of 10 to 500 nanometers; and detecting said complex in the lung of said subject, wherein the complex is produced in an aqueous medium comprising a pH selected to promote short-range attractive forces between the nanoparticle and the macromolecule by attenuating repulsive electrostatic forces, and wherein the complex accumulates in the lung and does not significantly accumulate in spleen or liver.

2. The method according to claim 1, wherein the macromolecule is poly-D-lysine.

3. The method according to claim 1, wherein the disease or condition is selected from the group consisting of pulmonary embolism, emphysema, chronic obstructive pulmonary disease (COPD), primary and metastatic lung tumours and infection.

4. The method of claim 1 wherein the aqueous medium is selected from the group consisting of:
 (a) an aqueous medium that comprises a pH at which the net charge on the macromolecule is substantially zero,
 (b) an aqueous medium that comprises a pH substantially equal to a pI of the macromolecule,
 (c) an aqueous medium that further comprises an electrolyte concentration selected to promote short-range attractive forces between the nanoparticles and the macromolecule by attenuating repulsive electrostatic forces, and
 (d) an aqueous medium that comprises a pH different than a pI of the macromolecule and a simple electrolyte concentration that is in a range of from greater than about 1 millimolar to about 150 millimolar.

5. The method of claim 4 wherein the simple electrolyte is selected from the group consisting of Na, K, and Ca.

6. The method of claim 1, wherein the method further comprises either (i) a step of separating the radiolabeled macromolecule complex from unlabeled macromolecule, or (ii) a step of separating the radiolabeled macromolecule complex from free nanoparticle composite.

7. The method of claim 1, wherein the radioactive particulate core comprises $^{99m}$Tc.

8. The method of claim 1 wherein the step of detecting comprises imaging by single photon computed tomography (SPECT) or positron emission tomography (PET).

* * * * *